United States Patent
Du Plessis et al.

(10) Patent No.: US 11,667,931 B2
(45) Date of Patent: Jun. 6, 2023

(54) AAV CAPSID PRODUCTION IN INSECT CELLS

(71) Applicant: uniQure IP B.V., Amsterdam (NL)

(72) Inventors: David Johannes Francois Du Plessis, Amsterdam (NL); Olivier Ter Brake, Amsterdam (NL); Sebastiaan Menno Bosma, Amsterdam (NL); Harald Peter Albert Petry, Amsterdam (NL); Jacek Lubelski, Amsterdam (NL)

(73) Assignee: uniQure IP B.V., Amsterdam (NL)

( * ) Notice: Subject to any disclaimer, the term of this patent is extended or adjusted under 35 U.S.C. 154(b) by 612 days.

(21) Appl. No.: 16/743,415

(22) Filed: Jan. 15, 2020

(65) Prior Publication Data
US 2020/0248206 A1    Aug. 6, 2020

Related U.S. Application Data

(63) Continuation of application No. PCT/EP2018/069704, filed on Jul. 20, 2018.

(30) Foreign Application Priority Data

Jul. 20, 2017 (EP) .................................... 17182429

(51) Int. Cl.
| | | |
|---|---|---|
| *C12N 15/86* | (2006.01) | |
| *C12N 7/00* | (2006.01) | |
| *C07K 14/005* | (2006.01) | |
| *C12N 5/07* | (2010.01) | |

(52) U.S. Cl.
CPC ............ *C12N 15/86* (2013.01); *C07K 14/005* (2013.01); *C12N 5/0601* (2013.01); *C12N 7/00* (2013.01); *C12N 2710/14043* (2013.01); *C12N 2750/14122* (2013.01)

(58) Field of Classification Search
None
See application file for complete search history.

(56) References Cited

U.S. PATENT DOCUMENTS

| | | |
|---|---|---|
| 2003/0148506 A1 | 8/2003 | Kotin et al. |
| 2004/0197895 A1 | 10/2004 | Kotin et al. |

FOREIGN PATENT DOCUMENTS

| | | |
|---|---|---|
| WO | WO-2007/046703 | 4/2007 |
| WO | WO-2007/148971 A2 | 12/2007 |
| WO | WO-2015/137802 | 9/2015 |

OTHER PUBLICATIONS

Clark, K. Reed, Recent advances in recombinant adeno-associated virus vector production, Kidney International, vol. 61, Symposium 1, S9-S15, 2002, 7 pages.
Haifeng Chen, Adeno-associated virus vectors for human gene therapy, World Journal of Medical Genetics, vol. 5, No. 3, dated Jan. 1, 2015, 19 pages.
Haifeng Chen, Intron Splicing-mediated Expression of AAV Rep and Cap Genes and Production of AAV Vectors in Insect Cells, Molecular Therapy, vol. 16, No. 5, dated May 1, 2008, 7 pages.
International Search Report and Written Opinion for International Application No. PCT/EP2018/069704, dated Sep. 9, 2018, 12 pages.
Lubelski et al., Insect Cell-Based Recombinant Adeno-Associated Virus Production: Molecular Process Optimization, Bioprocessing Journal, dated Jan. 1, 2014, 6 pages.
Urabe et al., Insect Cells as a Factory to Produce Adeno-Associated Virus Type 2 Vectors, Human Gene Therapy 13: 1935-1943, Nov. 1, 2002, 9 pages.
Urabe et al., Scalable Generation of High-Titer Recombinant Adeno-Associated Virus Type 5 in Insect Cells, Journal of Virology, vol. 80, No. 4, Feb. 2006, 12 pages.

*Primary Examiner* — Stacy B Chen
(74) *Attorney, Agent, or Firm* — Foley & Lardner LLP

(57) ABSTRACT

The present invention relates to the production of adeno-associated viral vectors in insect cells. The insect cells therefore comprise a first nucleotide sequence encoding the adeno-associated virus (AAV) capsid proteins, whereby the initiation codon for translation of the AAV VP1 capsid protein is an AUG. Upstream of the VP1 open reading frame an alternative out of frame start codon is placed such that translation initiation of the VP1 protein is modified, i.e. reduced, to allow production of VP1:VP2:VP3 in a good stoichiometry resulting in AAV with high potency.

13 Claims, 9 Drawing Sheets

Specification includes a Sequence Listing.

```
       CT NNN NNN XXX GNN NNN TTT
    1  CT CGA TGC ATG GTA AGC TTT
(a) 2  CT CGT GCC CTG GCT TCG TTT
       .
    n  CT TCC GCC GTG GCG TCG TTT
```

(b)

(c)

(d)

(e)

Figure 5A
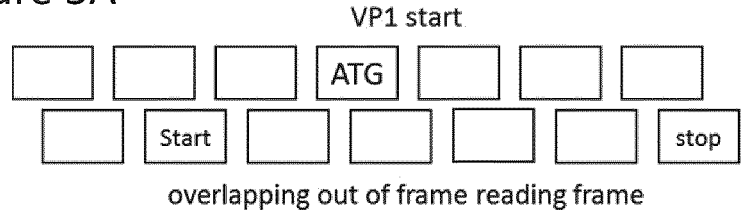
overlapping out of frame reading frame
Figure 5B
```
                        start
Cap - CT CGA TGC [ATG] GTA AGC TTT GTT GAT
OOF - CT CG[A TG]C ATG GTA AGC TTT GT[T GA]T
         start                          stop
```
Figure 5C
```
                        start
Cap - CT GAA TAC [ATG] GTC ACC TTT (N)
OOF - [CT G]AA TAC ATG GTC ACC TTT (N)A[TA G]
       start                              stop
```
```
                        start
Cap - CT GGA GAT [ATG] GTG AGT TTT GTT GAT
OOF - [CT G]GA GAT ATG G[TG A]GT TTT GTT GAT
       start            stop
```
Figure 5D
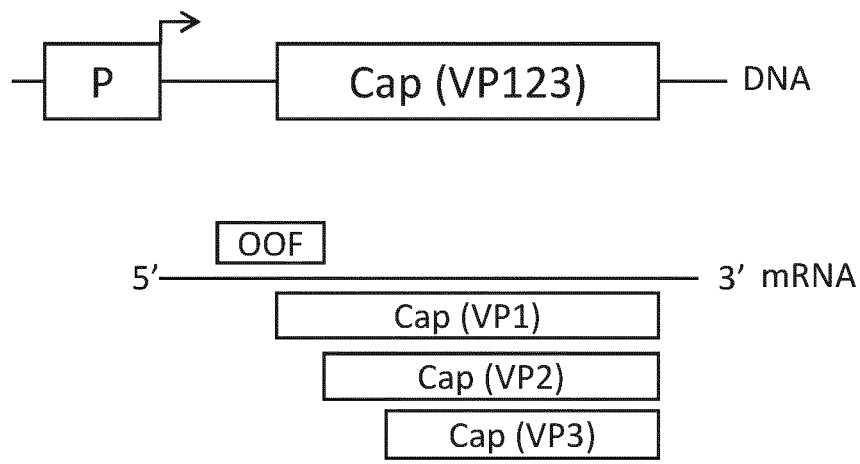

SEQUENCE LISTING

<160> NUMBER OF SEQ ID NOS: 74

<210> SEQ ID NO 1
<211> LENGTH: 20
<212> TYPE: DNA
<213> ORGANISM: Artificial Sequence
<220> FEATURE:
<223> OTHER INFORMATION: ATG containing sequence 1

<400> SEQUENCE: 1
ctcgatgcat ggtaagcttt                                            20

<210> SEQ ID NO 2
<211> LENGTH: 20
<212> TYPE: DNA
<213> ORGANISM: Artificial Sequence
<220> FEATURE:
<223> OTHER INFORMATION: ATG containing sequence 2

<400> SEQUENCE: 2
ctgaatacat ggtcaccttt                                            20

<210> SEQ ID NO 3
<211> LENGTH: 20
<212> TYPE: DNA
<213> ORGANISM: Artificial Sequence
<220> FEATURE:
<223> OTHER INFORMATION: ATG containing sequence 3

<400> SEQUENCE: 3
ctaacttaat ggtagcattt                                            20

<210> SEQ ID NO 4
<211> LENGTH: 20
<212> TYPE: DNA
<213> ORGANISM: Artificial Sequence
<220> FEATURE:
<223> OTHER INFORMATION: ATG containing sequence 4

<400> SEQUENCE: 4
ctcaatggat ggttagtttt                                            20

<210> SEQ ID NO 5
<211> LENGTH: 20
<212> TYPE: DNA
<213> ORGANISM: Artificial Sequence
<220> FEATURE:
<223> OTHER INFORMATION: ATG containing sequence 5

```
<400> SEQUENCE: 5
ctcgacgtat ggtcacattt                                              20

<210> SEQ ID NO 6
<211> LENGTH: 20
<212> TYPE: DNA
<213> ORGANISM: Artificial Sequence
<220> FEATURE:
<223> OTHER INFORMATION: ATG containing sequence 6

<400> SEQUENCE: 6
ctccctgaat ggcattgttt                                              20

<210> SEQ ID NO 7
<211> LENGTH: 20
<212> TYPE: DNA
<213> ORGANISM: Artificial Sequence
<220> FEATURE:
<223> OTHER INFORMATION: ATG containing sequence 7

<400> SEQUENCE: 7
ctagcacgat ggcgtcattt                                              20

<210> SEQ ID NO 8
<211> LENGTH: 20
<212> TYPE: DNA
<213> ORGANISM: Artificial Sequence
<220> FEATURE:
<223> OTHER INFORMATION: ATG containing sequence 8

<400> SEQUENCE: 8
ctgaccgcat ggcgacgttt                                              20

<210> SEQ ID NO 9
<211> LENGTH: 20
<212> TYPE: DNA
<213> ORGANISM: Artificial Sequence
<220> FEATURE:
<223> OTHER INFORMATION: ATG containing sequence 9

<400> SEQUENCE: 9
ctggagatat ggtgagtttt                                              20

<210> SEQ ID NO 10
<211> LENGTH: 20
<212> TYPE: DNA
<213> ORGANISM: Artificial Sequence
<220> FEATURE:
<223> OTHER INFORMATION: ATG containing sequence 10

<400> SEQUENCE: 10
cttgttttat ggtaagtttt                                              20

<210> SEQ ID NO 11
<211> LENGTH: 20
<212> TYPE: DNA
<213> ORGANISM: Artificial Sequence
<220> FEATURE:
<223> OTHER INFORMATION: ATG containing sequence 11

<400> SEQUENCE: 11
ctcagttgat ggtcagcttt                                              20

<210> SEQ ID NO 12
```

```
<211> LENGTH: 20
<212> TYPE: DNA
<213> ORGANISM: Artificial Sequence
<220> FEATURE:
<223> OTHER INFORMATION: ATG containing sequence 12

<400> SEQUENCE: 12
ctacttgtat ggtagctttt                                              20

<210> SEQ ID NO 13
<211> LENGTH: 20
<212> TYPE: DNA
<213> ORGANISM: Artificial Sequence
<220> FEATURE:
<223> OTHER INFORMATION: ATG containing sequence 13

<400> SEQUENCE: 13
ctcgatgcat ggcaagcttt                                              20

<210> SEQ ID NO 14
<211> LENGTH: 20
<212> TYPE: DNA
<213> ORGANISM: Artificial Sequence
<220> FEATURE:
<223> OTHER INFORMATION: ATG containing sequence 14

<400> SEQUENCE: 14
ctgttagaat ggcgacgttt                                              20

<210> SEQ ID NO 15
<211> LENGTH: 20
<212> TYPE: DNA
<213> ORGANISM: Artificial Sequence
<220> FEATURE:
<223> OTHER INFORMATION: ATG containing sequence 15

<400> SEQUENCE: 15
ctcgaccaat gggaacgttt                                              20

<210> SEQ ID NO 16
<211> LENGTH: 20
<212> TYPE: DNA
<213> ORGANISM: Artificial Sequence
<220> FEATURE:
<223> OTHER INFORMATION: ATG containing sequence 16

<400> SEQUENCE: 16
ctggcgtcat ggggtcgttt                                              20

<210> SEQ ID NO 17
<211> LENGTH: 20
<212> TYPE: DNA
<213> ORGANISM: Artificial Sequence
<220> FEATURE:
<223> OTHER INFORMATION: ATG containing sequence 17

<400> SEQUENCE: 17
ctcgatgcat ggtaagctct                                              20

<210> SEQ ID NO 18
<211> LENGTH: 20
<212> TYPE: DNA
<213> ORGANISM: Artificial Sequence
<220> FEATURE:
<223> OTHER INFORMATION: ATG containing sequence 18

<400> SEQUENCE: 18
```

```
ctcgatgcat ggtgagcttt                                          20

<210> SEQ ID NO 19
<211> LENGTH: 20
<212> TYPE: DNA
<213> ORGANISM: Artificial Sequence
<220> FEATURE:
<223> OTHER INFORMATION: ATG containing sequence 19

<400> SEQUENCE: 19
ctcgatgcat ggtaagcctt                                          20

<210> SEQ ID NO 20
<211> LENGTH: 20
<212> TYPE: DNA
<213> ORGANISM: Artificial Sequence
<220> FEATURE:
<223> OTHER INFORMATION: ATG containing sequence 20

<400> SEQUENCE: 20
ctcctcggat ggcgtcattt                                          20

<210> SEQ ID NO 21
<211> LENGTH: 20
<212> TYPE: DNA
<213> ORGANISM: Artificial Sequence
<220> FEATURE:
<223> OTHER INFORMATION: ATG containing sequence 21

<400> SEQUENCE: 21
cttgggcgat ggtttcattt                                          20

<210> SEQ ID NO 22
<211> LENGTH: 20
<212> TYPE: DNA
<213> ORGANISM: Artificial Sequence
<220> FEATURE:
<223> OTHER INFORMATION: ATG containing sequence 22

<400> SEQUENCE: 22
ctaattgaat ggcggagttt                                          20

<210> SEQ ID NO 23
<211> LENGTH: 20
<212> TYPE: DNA
<213> ORGANISM: Artificial Sequence
<220> FEATURE:
<223> OTHER INFORMATION: ATG containing sequence 23

<400> SEQUENCE: 23
ctcgatgcat ggtaggcttt                                          20

<210> SEQ ID NO 24
<211> LENGTH: 20
<212> TYPE: DNA
<213> ORGANISM: Artificial Sequence
<220> FEATURE:
<223> OTHER INFORMATION: ATG containing sequence 24

<400> SEQUENCE: 24
ctcgatgcat ggtaagcttc                                          20

<210> SEQ ID NO 25
<211> LENGTH: 20
<212> TYPE: DNA
```

<213> ORGANISM: Artificial Sequence
<220> FEATURE:
<223> OTHER INFORMATION: ATG containing sequence 25

<400> SEQUENCE: 25
ctttgcttat ggtaaatttt                                          20

<210> SEQ ID NO 26
<211> LENGTH: 20
<212> TYPE: DNA
<213> ORGANISM: Artificial Sequence
<220> FEATURE:
<223> OTHER INFORMATION: ATG containing sequence 26

<400> SEQUENCE: 26
ctcgacgcat ggtaagcttt                                          20

<210> SEQ ID NO 27
<211> LENGTH: 20
<212> TYPE: DNA
<213> ORGANISM: Artificial Sequence
<220> FEATURE:
<223> OTHER INFORMATION: ATG containing sequence 27

<400> SEQUENCE: 27
ctcacttgat ggcttaattt                                          20

<210> SEQ ID NO 28
<211> LENGTH: 20
<212> TYPE: DNA
<213> ORGANISM: Artificial Sequence
<220> FEATURE:
<223> OTHER INFORMATION: ATG containing sequence 28

<400> SEQUENCE: 28
ctcagggaat gggattcttt                                          20

<210> SEQ ID NO 29
<211> LENGTH: 20
<212> TYPE: DNA
<213> ORGANISM: Artificial Sequence
<220> FEATURE:
<223> OTHER INFORMATION: ATG containing sequence 29

<400> SEQUENCE: 29
cttattctat ggtaagtttt                                          20

<210> SEQ ID NO 30
<211> LENGTH: 20
<212> TYPE: DNA
<213> ORGANISM: Artificial Sequence
<220> FEATURE:
<223> OTHER INFORMATION: ATG containing sequence 30

<400> SEQUENCE: 30
ctcggtgcat ggtaagcttt                                          20

<210> SEQ ID NO 31
<211> LENGTH: 20
<212> TYPE: DNA
<213> ORGANISM: Artificial Sequence
<220> FEATURE:
<223> OTHER INFORMATION: ATG containing sequence ATG2

<400> SEQUENCE: 31
ctcgatgcat ggtaagcttt                                          20

<210> SEQ ID NO 32
<211> LENGTH: 20
<212> TYPE: RNA
<213> ORGANISM: Artificial Sequence
<220> FEATURE:
<223> OTHER INFORMATION: RNA sequence derived from ATG containing
      sequence 1

<400> SEQUENCE: 32
cucgaugcau gguaagcuuu                                              20

<210> SEQ ID NO 33
<211> LENGTH: 20
<212> TYPE: RNA
<213> ORGANISM: Artificial Sequence
<220> FEATURE:
<223> OTHER INFORMATION: RNA sequence derived from ATG containing
      sequence 2

<400> SEQUENCE: 33
cugaauacau ggucaccuuu                                              20

<210> SEQ ID NO 34
<211> LENGTH: 20
<212> TYPE: RNA
<213> ORGANISM: Artificial Sequence
<220> FEATURE:
<223> OTHER INFORMATION: RNA sequence derived from ATG containing
      sequence 3

<400> SEQUENCE: 34
cuaacuuaau gguagcauuu                                              20

<210> SEQ ID NO 35
<211> LENGTH: 20
<212> TYPE: RNA
<213> ORGANISM: Artificial Sequence
<220> FEATURE:
<223> OTHER INFORMATION: RNA sequence derived from ATG containing
      sequence 4

<400> SEQUENCE: 35
cucaauggau gguuaguuuu                                              20

<210> SEQ ID NO 36
<211> LENGTH: 20
<212> TYPE: RNA
<213> ORGANISM: Artificial Sequence
<220> FEATURE:
<223> OTHER INFORMATION: RNA sequence derived from ATG containing
      sequence 5

<400> SEQUENCE: 36
cucgacguau ggucacauuu                                              20

<210> SEQ ID NO 37
<211> LENGTH: 20
<212> TYPE: RNA
<213> ORGANISM: Artificial Sequence
<220> FEATURE:
<223> OTHER INFORMATION: RNA sequence derived from ATG containing
      sequence 6

<400> SEQUENCE: 37
cucccugaau ggcauuguuu                                              20

```
<210> SEQ ID NO 38
<211> LENGTH: 20
<212> TYPE: RNA
<213> ORGANISM: Artificial Sequence
<220> FEATURE:
<223> OTHER INFORMATION: RNA sequence derived from ATG containing
      sequence 7

<400> SEQUENCE: 38
cuagcacgau ggcgucauuu                                               20

<210> SEQ ID NO 39
<211> LENGTH: 20
<212> TYPE: RNA
<213> ORGANISM: Artificial Sequence
<220> FEATURE:
<223> OTHER INFORMATION: RNA sequence derived from ATG containing
      sequence 8

<400> SEQUENCE: 39
cugaccgcau ggcgacguuu                                               20

<210> SEQ ID NO 40
<211> LENGTH: 20
<212> TYPE: RNA
<213> ORGANISM: Artificial Sequence
<220> FEATURE:
<223> OTHER INFORMATION: RNA sequence derived from ATG containing
      sequence 9

<400> SEQUENCE: 40
cuggagauau ggugaguuuu                                               20

<210> SEQ ID NO 41
<211> LENGTH: 20
<212> TYPE: RNA
<213> ORGANISM: Artificial Sequence
<220> FEATURE:
<223> OTHER INFORMATION: RNA sequence derived from ATG containing
      sequence 10

<400> SEQUENCE: 41
cuuguuuuau gguaaguuuu                                               20

<210> SEQ ID NO 42
<211> LENGTH: 20
<212> TYPE: RNA
<213> ORGANISM: Artificial Sequence
<220> FEATURE:
<223> OTHER INFORMATION: RNA sequence derived from ATG containing
      sequence 11

<400> SEQUENCE: 42
cucaguugau ggucagcuuu                                               20

<210> SEQ ID NO 43
<211> LENGTH: 20
<212> TYPE: RNA
<213> ORGANISM: Artificial Sequence
<220> FEATURE:
<223> OTHER INFORMATION: RNA sequence derived from ATG containing
      sequence 12

<400> SEQUENCE: 43 cuacuugau gguagcuuuu                                                20
```

```
<210> SEQ ID NO 44
<211> LENGTH: 20
<212> TYPE: RNA
<213> ORGANISM: Artificial Sequence
<220> FEATURE:
<223> OTHER INFORMATION: RNA sequence derived from ATG containing
      sequence 13

<400> SEQUENCE: 44
cucgaugcau ggcaagcuuu                                                20

<210> SEQ ID NO 45
<211> LENGTH: 20
<212> TYPE: RNA
<213> ORGANISM: Artificial Sequence
<220> FEATURE:
<223> OTHER INFORMATION: RNA sequence derived from ATG containing
      sequence 14

<400> SEQUENCE: 45
cuguuagaau ggcgacguuu                                                20

<210> SEQ ID NO 46
<211> LENGTH: 20
<212> TYPE: RNA
<213> ORGANISM: Artificial Sequence
<220> FEATURE:
<223> OTHER INFORMATION: RNA sequence derived from ATG containing
      sequence 15

<400> SEQUENCE: 46
cucgaccaau gggaacguuu                                                20

<210> SEQ ID NO 47
<211> LENGTH: 20
<212> TYPE: RNA
<213> ORGANISM: Artificial Sequence
<220> FEATURE:
<223> OTHER INFORMATION: RNA sequence derived from ATG containing
      sequence 16

<400> SEQUENCE: 47
cuggcgucau ggggucguuu                                                20

<210> SEQ ID NO 48
<211> LENGTH: 20
<212> TYPE: RNA
<213> ORGANISM: Artificial Sequence
<220> FEATURE:
<223> OTHER INFORMATION: RNA sequence derived from ATG containing
      sequence 17

<400> SEQUENCE: 48
cucgaugcau gguaagcucu                                                20

<210> SEQ ID NO 49
<211> LENGTH: 20
<212> TYPE: RNA
<213> ORGANISM: Artificial Sequence
<220> FEATURE:
<223> OTHER INFORMATION: RNA sequence derived from ATG containing
      sequence 18

<400> SEQUENCE: 49
cucgaugcau ggugagcuuu                                                20

<210> SEQ ID NO 50
```

```
<211> LENGTH: 20
<212> TYPE: RNA
<213> ORGANISM: Artificial Sequence
<220> FEATURE:
<223> OTHER INFORMATION: RNA sequence derived from ATG containing
      sequence 19

<400> SEQUENCE: 50
cucgaugcau gguaagccuu                                                    20

<210> SEQ ID NO 51
<211> LENGTH: 20
<212> TYPE: RNA
<213> ORGANISM: Artificial Sequence
<220> FEATURE:
<223> OTHER INFORMATION: RNA sequence derived from ATG containing
      sequence 20

<400> SEQUENCE: 51
cuccucggau ggcgucauuu                                                    20

<210> SEQ ID NO 52
<211> LENGTH: 20
<212> TYPE: RNA
<213> ORGANISM: Artificial Sequence
<220> FEATURE:
<223> OTHER INFORMATION: RNA sequence derived from ATG containing
      sequence 21

<400> SEQUENCE: 52
cuugggcgau gguuucauuu                                                    20

<210> SEQ ID NO 53
<211> LENGTH: 20
<212> TYPE: RNA
<213> ORGANISM: Artificial Sequence
<220> FEATURE:
<223> OTHER INFORMATION: RNA sequence derived from ATG containing
      sequence 22

<400> SEQUENCE: 53
cuaauugaau ggcggaguuu                                                    20

<210> SEQ ID NO 54
<211> LENGTH: 20
<212> TYPE: RNA
<213> ORGANISM: Artificial Sequence
<220> FEATURE:
<223> OTHER INFORMATION: RNA sequence derived from ATG containing
      sequence 23

<400> SEQUENCE: 54
cucgaugcau gguaggcuuu                                                    20

<210> SEQ ID NO 55
<211> LENGTH: 20
<212> TYPE: RNA
<213> ORGANISM: Artificial Sequence
<220> FEATURE:
<223> OTHER INFORMATION: RNA sequence derived from ATG containing
      sequence 24

<400> SEQUENCE: 55
cucgaugcau gguaagcuuc                                                    20

<210> SEQ ID NO 56
<211> LENGTH: 20
```

```
<212> TYPE: RNA
<213> ORGANISM: Artificial Sequence
<220> FEATURE:
<223> OTHER INFORMATION: RNA sequence derived from ATG containing
      sequence 25

<400> SEQUENCE: 56
cuuugcuuau gguaaauuuu                                             20

<210> SEQ ID NO 57
<211> LENGTH: 20
<212> TYPE: RNA
<213> ORGANISM: Artificial Sequence
<220> FEATURE:
<223> OTHER INFORMATION: RNA sequence derived from ATG containing
      sequence 26

<400> SEQUENCE: 57
cucgacgcau gguaagcuuu                                             20

<210> SEQ ID NO 58
<211> LENGTH: 20
<212> TYPE: RNA
<213> ORGANISM: Artificial Sequence
<220> FEATURE:
<223> OTHER INFORMATION: RNA sequence derived from ATG containing
      sequence 27

<400> SEQUENCE: 58
cucacuugau ggcuuaauuu                                             20

<210> SEQ ID NO 59
<211> LENGTH: 20
<212> TYPE: RNA
<213> ORGANISM: Artificial Sequence
<220> FEATURE:
<223> OTHER INFORMATION: RNA sequence derived from ATG containing
      sequence 28

<400> SEQUENCE: 59
cucagggaau gggauucuuu                                             20

<210> SEQ ID NO 60
<211> LENGTH: 20
<212> TYPE: RNA
<213> ORGANISM: Artificial Sequence
<220> FEATURE:
<223> OTHER INFORMATION: RNA sequence derived from ATG containing
      sequence 29

<400> SEQUENCE: 60
cuuauucuau gguaaguuuu                                             20

<210> SEQ ID NO 61
<211> LENGTH: 20
<212> TYPE: RNA
<213> ORGANISM: Artificial Sequence
<220> FEATURE:
<223> OTHER INFORMATION: RNA sequence derived from ATG containing
      sequence 30

<400> SEQUENCE: 61
cucggugcau gguaagcuuu                                             20

<210> SEQ ID NO 62
<211> LENGTH: 20
<212> TYPE: RNA
```

```
<213> ORGANISM: Artificial Sequence
<220> FEATURE:
<223> OTHER INFORMATION: RNA sequence derived from ATG containing
      sequence ATG2

<400> SEQUENCE: 62
cugucgucau ggugucguuu                                            20

<210> SEQ ID NO 63
<211> LENGTH: 20
<212> TYPE: DNA
<213> ORGANISM: Artificial Sequence
<220> FEATURE:
<223> OTHER INFORMATION: CTG1

<400> SEQUENCE: 63
ctcgtgccct ggcttcgttt                                            20

<210> SEQ ID NO 64
<211> LENGTH: 20
<212> TYPE: DNA
<213> ORGANISM: Artificial Sequence
<220> FEATURE:
<223> OTHER INFORMATION: CTG2

<400> SEQUENCE: 64
cttgatgtct ggccactttt                                            20

<210> SEQ ID NO 65
<211> LENGTH: 20
<212> TYPE: DNA
<213> ORGANISM: Artificial Sequence
<220> FEATURE:
<223> OTHER INFORMATION: CTG1

<400> SEQUENCE: 65
cttccactgt ggcctccttt                                            20

<210> SEQ ID NO 66
<211> LENGTH: 20
<212> TYPE: DNA
<213> ORGANISM: Artificial Sequence
<220> FEATURE:
<223> OTHER INFORMATION: CTG2

<400> SEQUENCE: 66
cttccgccgt ggcgtcgttt                                            20

<210> SEQ ID NO 67
<211> LENGTH: 20
<212> TYPE: DNA
<213> ORGANISM: Artificial Sequence
<220> FEATURE:
<223> OTHER INFORMATION: TAG1

<400> SEQUENCE: 67
ctgcccccta ggaccgtttt                                            20

<210> SEQ ID NO 68
<211> LENGTH: 20
<212> TYPE: DNA
<213> ORGANISM: Artificial Sequence
<220> FEATURE:
<223> OTHER INFORMATION: TGA1

<400> SEQUENCE: 68
```
cttcaccctg agcgcaattt                                                     20

<210> SEQ ID NO 69
<211> LENGTH: 20
<212> TYPE: DNA
<213> ORGANISM: Artificial Sequence
<220> FEATURE:
<223> OTHER INFORMATION: Construct
<220> FEATURE:
<221> NAME/KEY: misc_feature
<222> LOCATION: (3)..(8)
<223> OTHER INFORMATION: n is a, c, g, or t
<220> FEATURE:
<221> NAME/KEY: misc_feature
<222> LOCATION: (13)..(17)
<223> OTHER INFORMATION: n is a, c, g, or t

<400> SEQUENCE: 69
ctnnnnnnat ggnnnnnttt                                                     20

<210> SEQ ID NO 70
<211> LENGTH: 2622
<212> TYPE: DNA
<213> ORGANISM: Artificial Sequence
<220> FEATURE:
<223> OTHER INFORMATION: AAV5 expression construct sequence
<220> FEATURE:
<221> NAME/KEY: promoter
<222> LOCATION: (1)..(155)
<223> OTHER INFORMATION: Polyhedrin Promoter
<220> FEATURE:
<221> NAME/KEY: misc_feature
<222> LOCATION: (105)..(112)
<223> OTHER INFORMATION: Transcriptional start
<220> FEATURE:
<221> NAME/KEY: misc_feature
<222> LOCATION: (105)..(2622)
<223> OTHER INFORMATION: mRNA transcript
<220> FEATURE:
<221> NAME/KEY: misc_feature
<222> LOCATION: (156)..(158)
<223> OTHER INFORMATION: Translational startcodon VP1
<220> FEATURE:
<221> NAME/KEY: misc_feature
<222> LOCATION: (156)..(2333)
<223> OTHER INFORMATION: CDS ORF: AAV5 Capsid
<220> FEATURE:
<221> NAME/KEY: polyA_signal
<222> LOCATION: (2382)..(2622)
<223> OTHER INFORMATION: poly A

<400> SEQUENCE: 70
tgtaatgaga cgcacaaact aatatcacaa actggaaatg tctatcaata tatagttgct        60
gatatcatgg agataattaa aatgataacc atctcgcaaa taaataagta ttttactgtt       120
ttcgtaacag ttttgtaata aaaaaaccta taaatatggt ctcttttgtt gatcacccac       180
ccgattggtt ggaagaagtt ggtgaaggtc ttcgcgagtt tttgggcctt gaagcgggcc       240
caccgaaacc aaaacccaat cagcagcatc aagatcaagc ccgtggtctt gtgctgcctg       300
gttataacta tctcggaccc ggaaacggtc tcgatcgagg agagcctgtc aacagggcag       360
acgaggtcgc gcgagagcac gacatctcgt acaacgagca gcttgaggcg ggagacaacc       420
cctacctcaa gtacaaccac gcggacgccg agtttcagga agctcgcc gacgacacat        480 ccttcggggg aaacctcgga aaggcagtct ttcaggccaa gaaagggt ctcgaacctt         540 ttggcctggt tgaagagggt gctaagacgg cccctaccgg aaagcggata gacgaccact       600
ttccaaaaag aaagaaggct cggacgaag aggactccaa gccttccacc tcgtcagacg        660
ccgaagctgg acccagcgga tcccagcagc tgcaaatccc agcccaacca gcctcaagtt       720

```
tgggagctga tacaatgtct gcgggaggtg gcggcccatt gggcgacaat aaccaaggtg      780
ccgatggagt gggcaatgcc tcgggagatt ggcattgcga ttccacgtgg atggggaca       840 gagtcgtcac caagtccacc cgaacctggg tgctgcccag ctacaacaac caccagtacc      900
gagagatcaa aagcggctcc gtcgacggaa gcaacgccaa cgcctacttt ggatacagca      960 cccccctgggg gtactttgac tttaaccgct tccacagcca ctggagcccc cgagactggc    1020
aaagactcat caacaactac tggggcttca gaccccggtc cctcagagtc aaaatcttca     1080
acattcaagt caaagaggtc acggtgcagg actccaccac caccatcgcc aacaacctca     1140
cctccaccgt ccaagtgttt acggacgacg actaccagct gccctacgtc gtcggcaacg     1200
ggaccgaggg atgcctgccg gccttccctc cgcaggtctt tacgctgccg cagtacggtt     1260
acgcgacgct gaaccgcgac aacacagaaa atcccaccga gaggagcagc ttcttctgcc    1320
tagagtactt tcccagcaag atgctgagaa cgggcaacaa ctttgagttt acctacaact     1380
ttgaggaggt gcccttccac tccagcttcg ctcccagtca gaacctgttc aagctggcca    1440
acccgctggt ggaccagtac ttgtaccgct tcgtgagcac aaataacact ggcggagtcc     1500
agttcaacaa gaacctggcc gggagatacg ccaacaccta caaaaactgg ttcccgggac    1560
ccatgggccg aacccagggc tggaacctgg gctccggggt caaccgcgcc agtgtcagcg     1620
ccttcgccac gaccaatagg atggagctcg agggcgcgag ttaccaggtg cccccgcagc    1680
cgaacggcat gaccaacaac ctccagggca gcaacaccta tgccctggag aacactatga    1740
tcttcaacag ccagccggcg aacccgggca ccaccgccac gtacctcgag ggcaacatgc    1800
tcatcaccag cgagagcgag acgcagccgg tgaaccgcgt ggcgtacaac gtcggcgggc    1860
agatggccac caacaaccag agctccacca ctgcccccgc gaccggcacg tacaacctcc    1920
aggaaatcgt gcccggcagc gtgtggatgg agagggacgt gtacctccaa ggacccatct    1980
gggccaagat cccagagacg ggggcgcact tcaccccctc tccggccatg gcggattcg    2040 gactcaaaca cccaccgccc atgatgctca tcaagaacac gcctgtgccc ggaaatatca    2100
ccagcttctc ggacgtgccc gtcagcagct tcatcaccca gtacagcacc gggcaggtca    2160
ccgtggagat ggagtgggag ctcaagaagg aaaactccaa gaggtggaac ccagagatcc    2220
agtacacaaa caactacaac gacccccagt tgtggactt tgccccggac agcaccgggg    2280
aatacagaac caccagacct atcggaaccc gataccttac ccgaccccett taatctagag    2340 cctgcagtct cgacaagcta gcttgtcgag aagtactaga ggatcataat cagccatacc    2400
acatttgtag aggttttact tgcttttaaaa aacctcccac acctccccct gaacctgaaa    2460
cataaaatga atgcaattgt tgttgttaac ttgtttattg cagcttataa tggttacaaa    2520
taaagcaata gcatcacaaa tttcacaaat aaagcatttt tttcactgca ttctagttgt    2580
ggtttgtcca aactcatcaa tgtatcttat catgtctgga tc                       2622
```

<210> SEQ ID NO 71
<211> LENGTH: 20
<212> TYPE: DNA
<213> ORGANISM: Artificial Sequence
<220> FEATURE:
<223> OTHER INFORMATION: Construct
<220> FEATURE:
<221> NAME/KEY: misc_feature
<222> LOCATION: (3)..(11)
<223> OTHER INFORMATION: n is a, c, g, or t
<220> FEATURE:
<221> NAME/KEY: misc_feature
<222> LOCATION: (9)..(9)

```
<223> OTHER INFORMATION: N is part of a start codon and can be any of a,
      c, t, or g
<220> FEATURE:
<221> NAME/KEY: misc_feature
<222> LOCATION: (10)..(10)
<223> OTHER INFORMATION: N is part of a start codon and can be any of t,
      g, or a
<220> FEATURE:
<221> NAME/KEY: misc_feature
<222> LOCATION: (11)..(11)
<223> OTHER INFORMATION: N is part of a start codon and can be any of a,
      c, t, or g
<220> FEATURE:
<221> NAME/KEY: misc_feature
<222> LOCATION: (13)..(17)
<223> OTHER INFORMATION: n is a, c, g, or t

<400> SEQUENCE: 71
ctnnnnnnnn ngnnnnnttt                                             20

<210> SEQ ID NO 72
<211> LENGTH: 6
<212> TYPE: PRT
<213> ORGANISM: Artificial Sequence
<220> FEATURE:
<223> OTHER INFORMATION: amino acid sequence 1

<400> SEQUENCE: 72

Met His His Gly Lys Leu
1               5

<210> SEQ ID NO 73
<211> LENGTH: 4
<212> TYPE: PRT
<213> ORGANISM: Artificial Sequence
<220> FEATURE:
<223> OTHER INFORMATION: Amino acid sequence 2

<400> SEQUENCE: 73

Met Glu Ile Trp
1

<210> SEQ ID NO 74
<211> LENGTH: 20
<212> TYPE: DNA
<213> ORGANISM: Artificial Sequence
<220> FEATURE:
<223> OTHER INFORMATION: ATG containing sequence derived from SEQ ID
      NO:70

<400> SEQUENCE: 74
ctataaatat ggtctctttt                                             20
```

AAV CAPSID PRODUCTION IN INSECT CELLS

CROSS-REFERENCE TO RELATED APPLICATIONS

This application is a continuation of International Application No. PCT/EP2018/069704, filed on Jul. 20, 2018, which claims the benefit of and priority to European Application No. 17182429.5, filed on Jul. 20, 2017, both of which are hereby incorporated by reference herein in their entireties.

SEQUENCE LISTING

This application contains a Sequence Listing which has been filed electronically in ASCII format and is hereby incorporated by reference in its entirety. The ASCII copy, created on Jan. 15, 2020, is named P6064534PCT_Sequence_Listing.txt and is 20 kilobytes in size.

FIELD OF THE INVENTION

The present invention relates to the production of adeno-associated virus in insect cells and to adeno-associated virus that provides improved infectivity. The present invention also relates to means and methods involving adeno-associated virus vector libraries.

BACKGROUND OF THE INVENTION

Adeno-associated virus (AAV) may be considered as one of the most promising viral vectors for human gene therapy. AAV has the ability to efficiently infect dividing as well as non-dividing human cells, the AAV viral genome integrates into a single chromosomal site in the host cell's genome, and most importantly, even though AAV is present in many humans it has never been associated with any disease. In view of these advantages, recombinant adeno-associated virus (rAAV) is being evaluated in gene therapy clinical trials for hemophilia B, malignant melanoma, cystic fibrosis, and other diseases. Numerous clinical trials and approval of gene therapy medicines in Europe, such as Alipogene tiparvovec (Glybera®, uniQure), holds a promise for AAV to become main stay of clinical practice.

In general, there are two main types of production systems for recombinant AAV. On the one hand there are conventional production systems in mammalian cell types (such as 293 cells, COS cells, HeLa cells, KB cells) and on the other hand production systems using insect cells.

The mammalian production system suffers from several drawbacks, which may include the limited number of rAAV particles generated per cell (order of $10^4$ particles (reviewed in Clark, 2002, Kidney Int. 61(Suppl. 1): 9-15) and cumbersome large scale manufacturing. For a clinical study, more than $10^{15}$ particles of rAAV may be required. To produce this number of rAAV particles, transfection and culture with approximately $10^{11}$ cultured human 293 cells, the equivalent of 5,000 175-cm² flasks of cells, would be required, which means transfecting up to $10^{11}$ 293 cells. Therefore, large scale production of rAAV using mammalian cell culture systems to obtain material for clinical trials has already proven to be problematic, production at a large commercial scale may not even be feasible. Furthermore, there is always the risk, that a vector for clinical use that is produced in a mammalian cell culture will be contaminated with undesirable, perhaps pathogenic, material present in the mammalian host cell.

To overcome these problems of mammalian productions systems, an AAV production system has been developed using insect cells (Urabe et al., 2002, Hum. Gene Ther. 13: 1935-1943; US 20030148506 and US 20040197895). AAV wild-type capsids from the wild-type virus consist of about 60 capsid proteins, i.e. VP1, VP2 and VP3 in a stoichiometry of about 1:1:10. Without being bound by theory, it is believed that the stoichiometry is important to achieve good potency for recombinant AAV, i.e. good transduction. In the wild-type virus, i.e. in mammalian cells, achieving a stoichiometry of about 1:1:10 of the three AAV capsid proteins (VP1, VP2 and VP3), relies on a combination of alternate usage of two splice acceptor sites and the less optimal utilization of an ACG initiation codon for VP2. However, for production of AAV in insect cells modifications were necessary because the expression strategy as it occurs in mammalian cells does not reproduce in insect cells. To obtain an improved production of capsid proteins in insect cells Urabe et al. (2002, supra) used a construct that is transcribed into a single polycistronic messenger that is able to express all three VP proteins without requiring splicing and wherein the first translation initiation codon is replaced by the codon ACG. WO2007/046703 discloses a further improvement of the infectivity of baculovirus-produced rAAV vectors by further optimizing the ratio of AAV capsid proteins in insect cells.

Urabe et al. (J. Virol., 2006, 80(4):1874-1885) reported that AAV5 particles produced in the baculovirus system using ACG as initiation codon of the VP1 capsid protein have a poor transduction efficiency or potency and that—in contrast to AAV2 with VP1 expressed from an ACG initiation codon—mutating the +4 position to a G-residue in the AAV5 VP1 coding sequence did not improve infectivity. Urabe et al. constructed chimeric AAV2/5 VP1 proteins, wherein the N-terminal portion of at least 49 amino acids of AAV5 VP1 was replaced with the corresponding part of AAV2 VP1 which improved transduction properties of the virions.

In a further approach, the expression of AAV capsid proteins was improved by inserting in the AAV capsid coding sequence one or more amino acid residues between the suboptimal (non-ATG) translation initiation codon and the codon encoding the amino acid residue that corresponds to the amino acid residue at position 2 of the wild type capsid amino acid sequence (Lubelski et al. WO2015137802).

Despite improvements to insect cell based production of capsids for manufacturing of AAV gene therapy vectors for use in medical treatments, there is still a need to further improve AAV capsid production and to provide for new methods to select for improved AAV capsid constructs for expression in insect cells.

DESCRIPTION OF THE INVENTION

Brief Description of the Invention

The current inventors have surprisingly found that AAV capsids can be highly efficiently produced in insect cells from an expression construct encoding a transcript for the VP1, VP2, and VP3 proteins from overlapping reading frames, wherein VP1 is translated from an AUG initiation codon. Constructs of the prior art containing an ATG initiation codon do not produce a ratio of VP1:VP2:VP3 like observed in wild-type AAV of about 1:1:10 and therefore, without being bound by theory, do not produce potent AAV. The expression constructs identified in the current invention allow for efficient production in insect cells of good quantities of highly potent AAV gene therapy vectors for use in medical treatments. Such vectors are at least similar if not improved with regard to potency and quantity over AAV gene therapy vectors produced from alternative start codons such as CTG or GTG (see FIGS. 4A-4B).

Accordingly, the constructs of the invention contain an additional out of frame start codon 5' from the VP1 ATG start codon that apparently results in a reduction of translation initiation at the VP1 start codon allowing translation of sufficient quantities of VP1, VP2 and VP3. Without being bound by theory, such constructs may allow for the expression of VP1, VP2 and VP3 amino acid sequences as they are found in the wild-type virus.

As shown in the examples, such constructs were identified by using a library of AAV capsid expression constructs for insect cells. Constructs were selected requiring first highly efficient production of AAV capsids in insect cells and secondly requiring to be highly infectious on selected target cells. Hence, the current inventors also provide for a highly efficient selection method to provide for AAV capsid expression constructs having improved properties, e.g. improved production and/or improved infectivity.

Hence, in a first aspect, in the present invention a nucleic acid construct is provided comprising expression control sequences for expression in an insect cell of a nucleotide sequence comprising an open reading frame, wherein the open reading frame sequence encodes:
  i) adeno-associated virus (AAV) capsid proteins VP1, VP2 and VP3; and
  ii) an AUG translation initiation codon for VP1;
wherein said nucleotide sequence comprises upstream of the open reading frame an alternative start codon which is out of frame with the open reading frame. In other words, the alternative start codon is preferably 3N+1 or 3N+2 nucleotides upstream of the start codon.

In another aspect, the invention provides for a method for providing a nucleic acid construct encoding a parvoviral capsid protein for production in insect cells, said nucleic acid construct having one or more improved properties, which method comprises:
a) providing a plurality of nucleic acid constructs, each construct comprising:
a nucleotide sequence encoding a parvoviral capsid protein operably linked to an expression control sequence and at least one parvoviral inverted terminal repeat (ITR) sequence flanking said nucleotide sequence encoding a parvoviral capsid protein operably linked to an expression control sequence;
b) transferring the plurality of nucleic acid constructs into insect cells which are capable of expressing parvoviral Rep protein;
c) subjecting the insect cells to conditions to allow for expression of parvoviral capsid protein and the parvoviral rep protein so that the nucleic acid constructs can be packaged into parvoviral capsids to provide for parvoviral virions;
d) recovering parvoviral virions from the insect cells and/or insect cell supernatant;
e) contacting said parvoviral virions with a target cell to allow for infection of the target cell;
f) recovering the nucleic acid constructs from the target cells.

Hence, combined, steps (c) and (e) allows to select for capsid expression constructs that allow for efficient production in insect cells and which produce infectious virions on the target cell. Selected expression constructs that dominate the population may be in particular suitable candidates. Selected candidate expression constructs (without flanking ITRs) can subsequently be used, e.g. in a baculovirus vector or inserted in a cell line, to produce AAV gene therapy vectors.

FIGS. 2A-2E: In these plots the percentage (y-axis) of library members having a particular start codon (x-axis) is shown at each stage of the selection process; A) This plot shows the distribution of start codons of the plasmid DNA library that was made having the expression cassettes flanked by AAV ITRs. The prevalence varies between about 4% to about 8%; B) This plot shows the distribution of start codons of the baculovirus library that was made with the inserted expression cassettes flanked by AAV ITRs. The prevalence varies between about 4% to about 9%, note that the distribution profile of this library is very similar to the plasmid library; C) This plot shows the distribution of start codons contained in the AAV library that was made from the baculovirus library of FIG. 2B). Note that the distribution of the start codons is very similar to the baculovirus library, ranging from about 4% to 9%, with one exception, i.e. the ATG start codon which has a prevalence of well below 0.5%; D) This plot shows the distribution of start codons contained in the AAV vector genome in cells that were infected with the AAV library of FIG. 2C). Note that the distribution of the start codons is now very different. CTG and GTG are the most prevalent start codons having a prevalence of about 50%. The start codon ATG which was poorly represented in the AAV library now has a prevalence of about 8%, whereas the remainder of start codons had a prevalence between about 1% and 3%; E) this plot combines the respective plots of FIGS. 2A)-D). Note the dip for the ATG codon for the AAV library and the peaks for CTG, GTG and ATG in the cell library.

Figure 3:
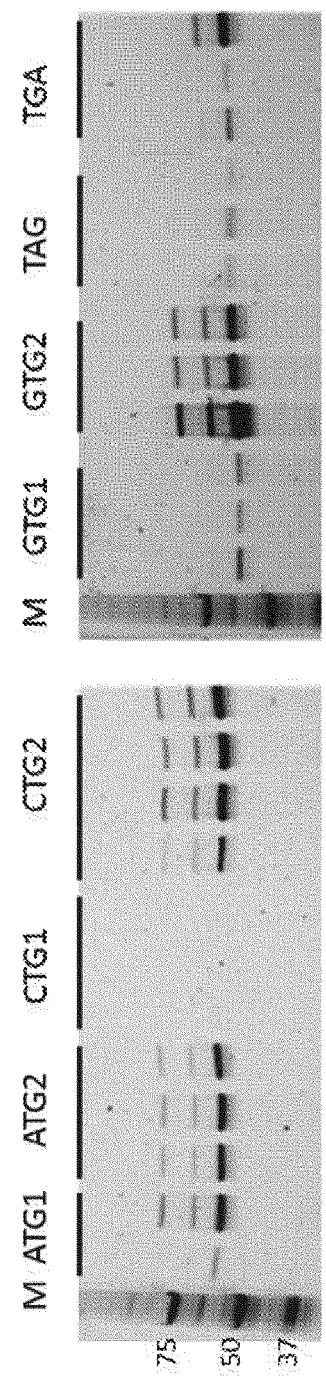

FIG. 3. Selected sequences (ATG1, ATG2 etc.) were subsequently cloned in a baculovirus vector for expression of AAV5 capsids. Clones of the baculovirus vectors were subsequently analysed by SDS-PAGE to assess VP1:VP2: VP3 ratio's. CTG1 did not produce good clones, while CTG2 and GTG2 did, displaying a stoichiometry as shown previously (Lubelski et al., WO2015137802). The TAG clones produced low titers and the TGA clones did not appear to produce VP1. Surprisingly, ATG1 and ATG2 produced good clones having a stoichiometry similar to CTG2.

Figure 4A:
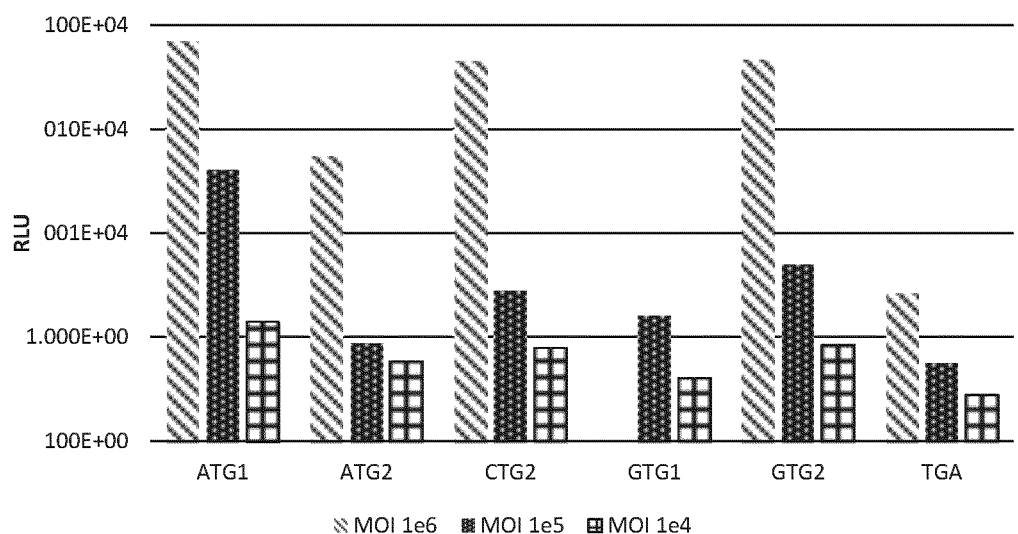
Figure 4B:
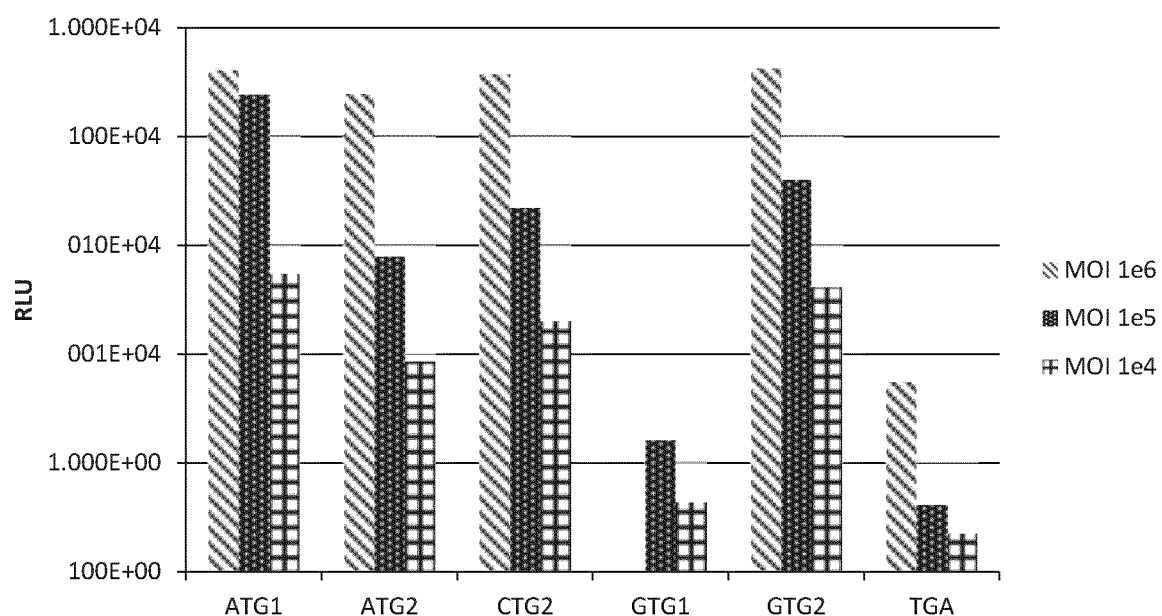

FIGS. 4A-4B. AAV potency assay. The relative potency of different AAV vectors carrying the SEAP reporter gene under control of the CMV promoter was tested in Huh7 cells (FIG. 4A) and HeLa cell (FIG. 4B). Cells were infected with different multiplicity of infections ($10^6$, $10^5$, $10^4$ genomic copies of AAV (gc) per cell) and expression of the SEAP reporter gene was determined. The ATG1 construct resulted the most potent vector, whereas ATG2, CTG2 and GTG2 had similar profiles, while TGA was significantly less potent because it did not, or hardly, contain any VP1 protein. The GTG1 AAV vector produced a low titer of gc/ml and hence did not allow for infection with an MOI of $10^6$.

FIGS. 5A-5D. Schematic of ATG sequence context for efficient AAV capsid protein expression.

FIG. 5A) The upper boxes show from left to right the codons in the open reading frame for VP1. The box with the VP1 start codon contains "ATG". The lower boxes are out of frame with the open reading frame for VP1. Upstream of the ATG codon is an alternative start codon (Start) and downstream thereof also a stop codon (stop). FIG. 5B) Shown is the sequence of the predominant sequence selected from the library (SEQ ID NO:1). In the out of frame overlapping reading frame (OOF) an ATG start codon is found upstream of the in frame reading frame for Cap. The OOF has a TGA downstream stop codon in the sequence originating from the wild-type AAV5 sequence which would result in a short peptide of 6 amino acids, MHHGK (SEQ ID NO:72), when translated from the OOF initiation codon; FIG. 5C) Shown are sequences from further out of frame overlapping reading frames from another upstream start codon. The upper situation has an out of frame CTG start codon (SEQ ID NO:2) with a stop codon further down the sequence originating from the AAV5 sequence (see i.a. SEQ ID NO:70). This would result in translation of a larger protein sequence of about 158 amino acids terminating at a TAG stop codon. The lower situation has also a CTG start codon with a stop codon in the mutated sequence just downstream of the start codon which would result in a short peptide of 4 amino acids, MEIW (SEQ ID NO:73), when translated from the OOF (SEQ ID NO:9); FIG. 5D) Schematic of expression of VP1, VP2 and VP3 capsid proteins from constructs as depicted in FIGS. 5A-C. The DNA contains an expression cassette with a promoter (P) and an open reading frame for capsid proteins (Cap(VP123)). Transcription initiation is indicated with the arrow. Transcription results in an mRNA from which first an OOF protein can be translated and subsequently VP1, VP2 and VP3 capsid proteins. The OOF sequence overlaps with the VP1 translation start.

Figure 6A:
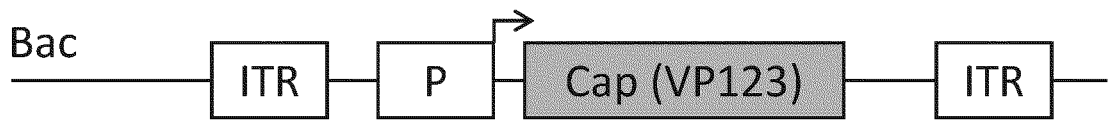
Figure 6A:
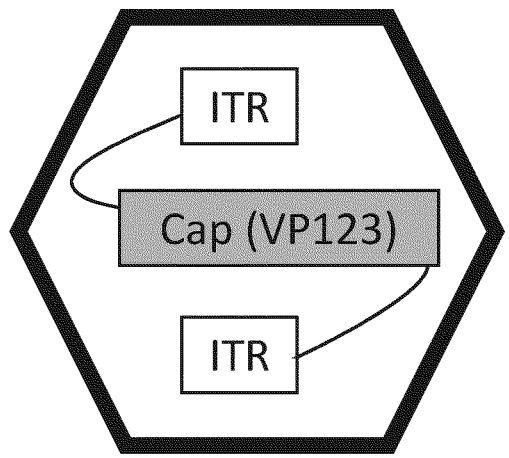
Figure 6B:
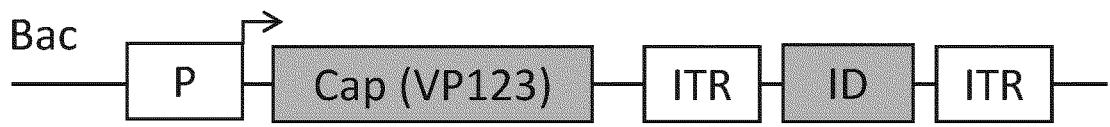
Figure 6B:
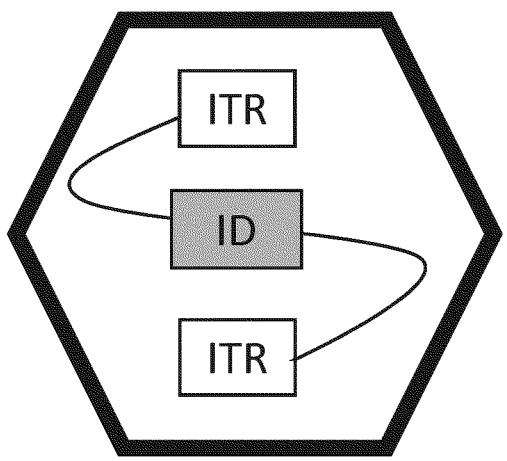
Figure 6C:
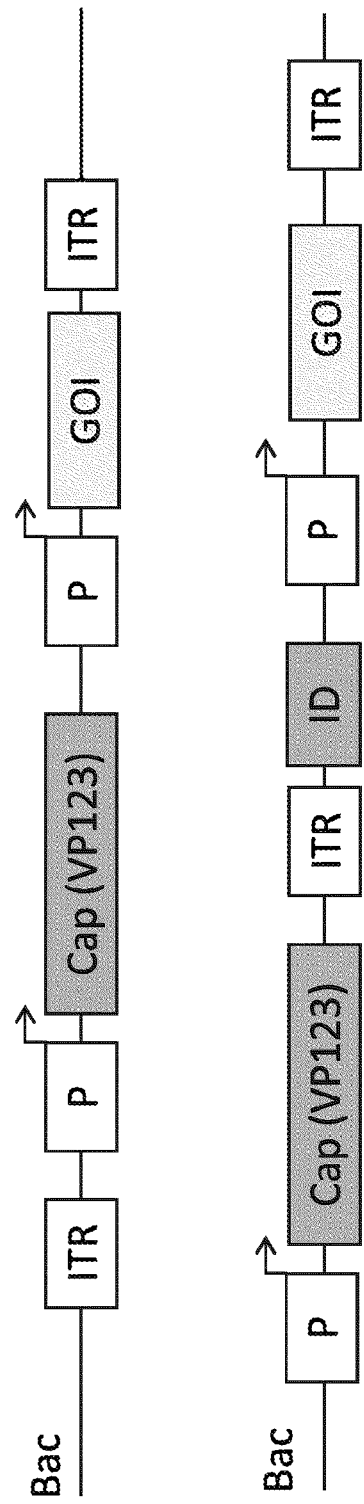

FIGS. 6A-6C. Schematic of various vector vehicle configurations for AAV library preparation. FIG. 6A: shown is the configuration as used in the examples wherein an expression cassette expressing AAV capsid proteins (grey box) is contained between AAV ITRs and within a Baculovirus genome. AAV produced therefrom contains the vector genome with ITRs flanking the expression cassette. FIG. 6B: shown is a configuration wherein a vector vehicle (e.g. Baculovirus) contains an expression cassette for parvovirus capsid proteins and wherein in between the vector genome ITR sequence a sequence identifier (ID) is placed. AAV produced therefrom contains the vector genome with ITRs flanking the sequence identifier. By identifying the sequence identifier, e.g. via sequencing, because the Cap sequence and ID are linked, the corresponding cap sequence, because the ID and Cap sequence are associated in one genome, can be determined, e.g. via sequencing of the Baculovirus vector that contains both or because the Baculovirus vector was constructed in such a way that a priori the identifier sequence and Cap expression sequence combination was known. FIG. 6C Constructs may also comprise a reporter gene within the parvoviral vector genome.

DEFINITIONS

As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signal for introns, and stop codons. The term "expression control sequence" is intended to include, at a minimum, a sequence whose presence are designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, sequences referred to as polyA sequences. It also can be designed to enhance mRNA stability. Expression control sequences which affect the transcription and translation stability, e.g., promoters, as well as sequences which effect the translation, e.g., Kozak sequences, are known in insect cells. Expression control sequences can be of such nature as to modulate the nucleotide sequence to which it is operably linked such that lower expression levels or higher expression levels are achieved.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer. A "tissue specific" promoter is only active in specific types of tissues or cells.

The terms "substantially identical", "substantial identity" or "essentially similar" or "essential similarity" means that two peptide or two nucleotide sequences, when optimally aligned, such as by the programs GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides, the default scoring matrix used is nwsgapdna and for proteins the default scoring matrix is Blosum62 (Henikoff & Henikoff, 1992, PNAS 89, 915-919). It is clear than when RNA sequences are said to be essentially similar or have a certain degree of sequence identity with DNA sequences, thymine (T) in the DNA sequence is considered equal to uracil (U) in the RNA sequence. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or the open-source software Emboss for Windows (current version 2.7.1-07). Alternatively, percent similarity or identity may be determined by searching against databases such as FASTA, BLAST, etc.

Nucleotide sequences encoding parvoviral Rep proteins or Cap proteins of the invention may also be defined by their capability to hybridize with their respective nucleotide sequences, under moderate, or preferably under stringent hybridization conditions. Stringent hybridization conditions are herein defined as conditions that allow a nucleic acid sequence of at least about 25, preferably about 50 nucleotides, 75 or 100 and most preferably of about 200 or more nucleotides, to hybridize at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridization is performed overnight, i.e. at least for 10 hours and preferably washing is performed for at least one hour with at least two changes of the washing solution. These conditions will usually allow the specific hybridization of sequences having about 90% or more sequence identity.

Moderate conditions are herein defined as conditions that allow a nucleic acid sequences of at least 50 nucleotides, preferably of about 200 or more nucleotides, to hybridize at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridization is performed overnight, i.e. at least for 10 hours, and preferably washing is performed for at least one hour with at least two changes of the washing solution. These conditions will usually allow the specific hybridization of sequences having up to 50% sequence identity. The person skilled in the art will be able to modify these hybridization conditions in order to specifically identify sequences varying in identity between 50% and 90%.

DETAILED DESCRIPTION OF THE INVENTION

The present invention relates to the use of animal parvoviruses, in particular dependoviruses such as infectious human or simian AAV, and the components thereof (e.g., an animal parvovirus genome) for use as vectors for introduction and/or expression of nucleic acids in mammalian cells. In particular, the invention relates to improvements in infectivity of such parvoviral vectors when produced in insect cells.

Viruses of the Parvoviridae family are small DNA animal viruses. Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture. The genus Dependovirus includes AAV, which normally infects humans (e.g., serotypes 1, 2, 3A, 3B, 4, 5, 6, 7, 8, 9, 10, 11, 12, 13) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience, the present invention is further exemplified and described herein by reference to AAV. It is however understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wtAAV infection in mammalian cells the Rep genes (i.e. Rep78 and Rep52) are expressed from the P5 promoter and the P19 promoter, respectively and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production. The three capsid proteins, VP1, VP2 and VP3 are expressed from a single VP reading frame from the p40 promoter. wtAAV infection in mammalian cells relies for the capsid proteins production on a combination of alternate usage of two splice acceptor sites and the suboptimal utilization of an ACG initiation codon for VP2.

In insect cells, expression of a transcript, i.e. mRNA, with an AAV open reading frame encoding VP1 (with an AUG start codon), VP2 and VP3 proteins normally does not produce VP1, VP2 and VP3 capsid proteins in a ratio of about 1:1:10 and an amount that results in potent AAV. Potency being defined herein as the ability of the AAV vector to transfer its vector genome to a target cell and allow for efficient expression of a transgene. The current inventors now surprisingly found that AAV capsids can be highly efficiently produced in insect cells from an expression construct encoding a transcript for the VP1, VP2, and VP3 proteins, wherein VP1 is translated from an AUG initiation codon.

The expression constructs identified in the current invention allow for efficient production in insect cells of good quantities of highly potent AAV gene therapy vectors for use in medical treatments. Such vectors are at least similar if not improved with regard to potency over AAV gene therapy vectors produced from alternative start codons such as CTG or GTG (FIGS. 4A-4B). It is understood that with regard to the nucleic acid sequences these can be listed either as a DNA sequence, listing A, T, C and G, or as an RNA sequence, listing A, U, C and G. It is understood that an expression construct usually may refer to DNA sequences, whereas expressed nucleotide sequences refer to RNA sequences, i.e. the mRNA that is transcribed or expressed from an expression construct.

The constructs of the invention encode an additional out of frame start codon 5' from the VP1 start codon that apparently results in a reduction of translation initiation at the VP1 start codon allowing further translation of sufficient quantities of both VP2 and VP3. Without being bound by theory, such out of frame 5' start codon results in interference with transcription initiation at the VP1 AUG start codon and allows for pseudo leaky ribosomal scanning similar to as occurs in wild-type AAV. Without being bound by theory, the synthesis of short peptides (e.g. translation termination of out of frame reading frame before VP2 encoding sequence) from these alternative start codons may allow the ribosome to continue scanning downstream of the VP1 AUG initiation codon or cause it to re-initiate, allowing for translation of the VP2 and VP3 from the same transcript.

Such constructs provide for at least similar, if not improved, production of AAV capsids in insect cells with good potency as compared with AAV capsids produced in the prior art. Advantageously, such constructs may allow for the VP1, VP2 and VP3 nucleotide sequences as they are found in the wild-type virus to be unmodified when utilized for the generation of expression constructs for insect cells. Constructs according to the invention may allow for the amino acid sequences for the VP1, VP2 and VP3 capsid proteins to be substantially identical to what capsid proteins found in wild-type virus or to be identical thereto. This expression strategy is therefore applicable in general for any parvoviral or AAV vector construct and may not require any further tailoring of 5' sequences or sequences of the AAV capsid open reading frames.

Hence, in a first aspect of the invention, a nucleic acid construct is provided comprising expression control sequences for expression in an insect cell of a nucleotide sequence comprising an open reading frame, wherein the open reading frame sequence encodes:
i) adeno-associated virus (AAV) capsid proteins VP1, VP2 and VP3; and
ii) an ATG translation initiation codon for VP1;
said nucleotide sequence comprising upstream of the open reading frame an alternative start codon which is out of frame with the open reading frame.

It is understood that the expression of a nucleotide sequence according to the invention relates to mRNA that is expressed. Hence, the alternative start codon is to be comprised in the mRNA, i.e. it is comprised in the sequence 5' from the open reading frame encoding the capsid proteins and it is 3' from the transcription initiation site of the nucleic acid construct. Said alternative reading frame is thus 5' from the VP1 AUG codon as comprised in the expressed mRNA. It is understood that with an open reading frame according to the invention is understood a single open reading frame, i.e. the sequences encoding the capsid proteins VP1, VP2 and VP3 are overlapping. In other words, the VP2 and VP3 proteins are encoded by the same sequence as the VP1 sequence. Such an open reading frame can be a contiguous open reading frame, but may also be not contiguous, e.g. containing an intron sequence. Preferably, said open reading frame from which VP1, VP2 and VP3 is being translated is a contiguous single open reading frame, wherein no further transcripts are transcribed in the insect from which capsid proteins can be translated (e.g. when one transcript encodes for VP1 and another transcript encodes for VP2, and still a further transcript encodes for VP3).

Said out of frame start codon is preferably selected from the group consisting of CUG, ACG, AUG, UUG, CUC and CUU. More preferably, the alternative start codon is selected from AUG or CUG. Most preferably, said alternative start codon is AUG. As shown in the example section, sequences having an AUG start codon that were most prevalent contained mostly an out of frame start codon. Mostly the upstream out of frame start codon is a relatively strong codon such as UUG, CUG, GUG, AUG and ACG. Weaker start codons such as CUC and CUU were also observed. Most prevalent and most preferred is the AUG as an out of frame alternative start codon.

The alternative start codon can be the start of an alternative open reading frame. Hence, an alternative start codon is understood to comprise a codon from which the ribosome can initiate translation. Sometimes when a start codon is e.g. close to the 5' capped end of an mRNA such a sequence may not be allowed to function as a start codon. It is understood that because of the genetic code, wherein a triplet encodes for an amino acid, a nucleic acid sequence can be translated into three different amino acid sequences depending on where translation initiates and terminates. The out of frame alternative start codons are upstream of the VP1 AUG initiation codon and preferably the genetic code following the alternative start codon is such that translation termination occurs such that the ribosome does not initiate, or is hampered to initiate, translation from the VP1 AUG initiation codon. Likewise, without being bound by theory, the out of frame alternative start codons upstream of the VP1 AUG initiation codon allow for initiation of translation from the mRNA. Preferably the alternative open reading frame terminates downstream of the VP1 AUG initiation codon. For example, when the VP1 AUG initiation codon would be immediately followed by an A, the UGA triplet in the AUGA sequence encodes for a termination codon. Hence, preferably, the alternative open reading frame, starting at the alternative start codon upstream encompasses the VP1 AUG start codon.

Therefore, in a further embodiment in accordance with the invention, a nucleic acid construct is provided for expression in an insect cell of a nucleotide sequence comprising an open reading frame, wherein the open reading frame sequence encodes adeno-associated virus (AAV) capsid proteins VP1, VP2 and VP3 and an AUG translation initiation codon for VP1, wherein said nucleotide sequence comprises an alternative open reading frame starting with an alternative start codon which alternative open reading frame encompasses said AUG translation initiation codon for VP1.

The alternative open reading frame initiates preferably at most 100, 90, 80, 70, 60, 50, 40, 30, 20, or 10 nucleotides 5' from the VP1 AUG start codon and terminates thereafter. The alternative open reading frame initiates 5' from the VP1 AUG start codon and terminates at most 500, 400, 300, 200, 150, 100, 90, 80, 70, 60, 50, 40, 30, 20, or 10 nucleotides thereafter. The alternative open reading frame can initiate at most 50 nucleotides 5' from the VP1 AUG start codon and terminates at most 500 nucleotides thereafter. The alternative open reading frame can initiate at most 40 nucleotides 5' from the VP1 AUG start codon and terminates at most 200 nucleotides thereafter. The alternative open reading frame can also initiate at most 30 nucleotides 5' from the VP1 AUG start codon and terminates at most 50 nucleotides thereafter. The alternative open reading frame can initiate at most 10 nucleotides from the VP1 AUG start codon and terminates at most 20 nucleotides thereafter. In one alternative embodiment, said alternative open reading frame terminates before the initiation codon of VP3, preferably before the initiation codon of VP2. For example, such alternative open reading frames shown in the examples, initiating at 4 nucleotides upstream and terminating 14 nucleotides thereafter, or initiating 8 nucleotides upstream and terminating 4 or more nucleotides thereafter.

Such alternative open reading frames may preferably be comprised in DNA sequence encoding adeno-associated virus (AAV) capsid proteins VP1, VP2 and VP3 comprising upstream of a VP1 ATG start codon sequence a sequence encoded by nucleotides 105-155 of the DNA sequence of SEQ ID NO:70. Said sequence upstream of the ATG start codon being transcribed in RNA. Such alternative open reading frames may also be comprised in DNA sequence encoding adeno-associated virus (AAV) capsid proteins VP1, VP2 and VP3 comprising upstream of a VP1 ATG start codon sequence a sequence encoded by nucleotides 1-155 of the DNA sequence of SEQ ID NO:70. Said upstream sequence encoding a polyhedrin promoter and 5' leader sequence upstream of the ATG VP1 start codon (105-155).

Hence, preferably, the alternative open reading frames of the invention as described above are translated in a peptide in the insect cells. In one embodiment, said peptide has a length of at least 4 amino acids, at least 5 amino acids, at least 6 amino acids. In one embodiment, the translated amino acid sequence comprises or consists of SEQ ID NO:72 or SEQ ID NO:73. In another embodiment, said peptide has a length of at most 200, 150, 100, 50, 40, 30, 20, or 10 amino acids. In a further embodiment, the nucleic acid constructs according to the invention encoding for said alternative open reading frames are translated into peptides with a length ranging from 2 to 200 amino acid, from 2 to 100, from 2 to 50 or, preferably, from 2 to 10. Hence, a nucleic acid construct according to the invention as described herein comprising said alternative open reading frame following the alternative start codon encodes a peptide. The length of the peptide may depend on the sequence after the VP1 start codon, i.e. the sequence encoding for VP1 that can e.g. be derived from an AAV sequence derived from nature, or from a synthetic or artificial AAV capsid sequence (e.g. codon optimized or a mutant variant with improved properties). Hence, the length depends on where a stop codon (TGA, TAA, TAG) occurs in the out of frame reading frame starting from the alternative start codon upstream of the VP1 ATG start codon. The sequence downstream of the start codon may be mutated to introduce a stop codon which is in frame with out of frame upstream start codon. This way, the length of the peptide may be purposely selected. One may thereby introduce an out of frame stop codon that with regard to the VP1 encoding sequence does not introduce a change in amino acid sequence, in other words, is a silent mutation in the VP1 reading frame. The introduced out of reading frame stop codon may be introduce by one, two or three point mutations in three consecutive nucleic acids in the reading frame. One may also insert a triplet sequence within the VP1 encoding sequence (i.e. TGA, TAA or TAG), which may result in an insertion of one amino acid with regard to the length of the encoding sequence and may result in an additional amino acid change of the VP1 encoding sequence (i.e. one triplet of the VP1 encoding sequence changes into two triplets by the insertion of the out of frame stop codon).

In another embodiment, a nucleic acid construct is provided comprising expression control sequences for expression in an insect cell of a nucleotide sequence comprising an open reading frame, wherein the open reading frame sequence encodes:
  i) adeno-associated virus (AAV) capsid proteins VP1, VP2 and VP3; and
  ii) an AUG translation initiation codon for VP1;
wherein said nucleotide sequence comprising directly upstream of the VP1 AUG nucleotides 1-8 of a nucleotide sequence selected from the group consisting of SEQ ID NOs. 32-62 It is understood that SEQ ID NOs. 32-62 refer to RNA sequences, hence the nucleic acid constructs will have corresponding DNA sequences encoding said RNA sequences such as listed in SEQ ID NOs. 1-31. Preferably, said nucleotide sequences comprise directly downstream of the VP1 AUG a G nucleotide. More preferably, the nucleic acid constructs according to the invention, comprise a sequence selected from the group consisting of SEQ ID NOs. 1-31 encoding for a VP1 start codon, wherein said VP1 start codon corresponds to position 9-11 of said SEQ ID NOs. 1-31. Most preferred are sequences derived from SEQ ID NO.1 and SEQ ID NO.32, i.e. preferably nucleotides 1-8 thereof, having preferably a G directly adjacent to the VP1 ATG, most preferably encoding for the entire sequence of either SEQ ID NO.1.

In a further embodiment, a nucleic acid construct according to invention is provided, wherein the second codon of the open reading frame of VP1 encodes an amino acid residue selected from the group consisting of alanine, glycine, valine, aspartic acid and glutamic acid. This second amino acid residue may be derived from an inserted codon in between the start codon and the second codon derived from e.g. a wild-type AAV VP1 sequence, or the second codon of the VP1 nucleotide sequence may be mutated codon (e.g. by mutating the nucleic acid immediately following the VP1 ATG codon into a G). Most preferably the second codon of VP1 encodes for a valine. More preferably, the second codon is selected from the group consisting of GUA, GUC, GUU, GUG, preferably the second codon is GUA. The open reading frame optionally comprises one or more codons encoding further additional amino acid residues following the second codon, for example codons for 1, 2, 3, 4, 5, 6, 7, 8, 9, 10, 11, 12, 13, 14, 15, 16, 17, 18, 19 or 20 additional amino acids, but preferably less than 60, 50, 40, 35, 30, 25, 20, 19, 18, 17, 16, 15 or 14 additional amino acid residues. As will be readily understood, the codons encoding the additional amino acid residues are to be in frame with the open reading frame of the capsid proteins.

Hence, in one embodiment, an AAV vector is provided comprising a VP1 capsid protein having a Valine at position 2 of VP1, either via modification of position 2 of a e.g. wild-type VP1 capsid protein sequence or via insertion of a Valine codon in between position 1 and position 2 of the wild-type VP1 capsid protein sequence, or because the VP1 capsid protein as found in nature or as selected already comprises a Valine at position 2. Such a capsid, as preferably produced in insect cells, may be in particular useful in a medical treatment as described herein.

In an embodiment, if the open reading frame is compared with a wild-type capsid protein, the open reading frame encoding the capsid proteins further comprises codons that encode for one or more amino acid residues inserted between the ATG translation initiation codon of VP1 and the codon that encodes for the amino acid residue immediately adjacent to the initiation codon on its 3' end in the corresponding wild-type capsid protein. For example, the open reading frame comprises codons for 1, 2, 3, 4, 5, 6, 7, 8, 9, 10, 11, 12, 13, 14, 15, 16, 17, 18, 19 or 20 additional amino acid residues as compared to the corresponding wild-type capsid protein. Preferably, the open reading frame comprises codons for less than 60, 50, 40, 35, 30, 25, 20, 19, 18, 17, 16, 15 or 14 additional amino acid residues as compared to the corresponding wild-type capsid protein. As will be readily understood, the codons encoding the additional amino acid residues are to be in frame with the open reading frame of the capsid proteins. Of these codons that encode the additional amino acid residues as compared to the corresponding wild-type capsid proteins, the first codon, i.e. the codon that is immediately adjacent to the suboptimal translation initiation codon at its 3' end, encodes for an amino acid residue selected from the group consisting of alanine, glycine, valine, aspartic acid and glutamic acid. Thus, if there is only one additional codon between the translation initiation codon and the codon that encodes for the amino acid residue that corresponds to residue 2 of the wild-type sequence, that additional codon encodes an amino acid residue selected from the group consisting of alanine, glycine, valine, aspartic acid and glutamic acid. If there are more than one additional codon between the translation initiation codon and the codon that encodes for amino acid residue 2 of the wild-type sequence, then the codon immediately following the translation initiation codon encodes an amino acid residue selected from the group consisting of alanine, glycine, valine, aspartic acid and glutamic acid. Preferably, the additional amino acid residue immediately following the suboptimal translation initiation codon (i.e. at its 3' end) is valine. In other words, in a preferred embodiment of the present invention, the codon immediately following the suboptimal translation initiation codon encodes valine.

The sequence encoding AAV capsid proteins in step a) can be a capsid sequence as found in nature such as for example of AAV1-AAV13 of which nucleotide and amino acid sequences are listed in Lubelski et al. WO2015137802 as SEQ ID NO: 13-38, which is incorporated herein in its entirety by reference. Hence, the nucleic acid construct according to the present invention can comprise an entire open reading frame for AAV capsid proteins as disclosed by Lubelski et al. WO2015137802. Alternatively, the sequence can be man-made, for example, the sequence may be a hybrid form or may be codon optimized, such as for example by codon usage of AcmNPv or *Spodoptera frugiperda*. For example, the capsid sequence may be composed of the VP2 and VP3 sequences of AAV1 whereas the remainder of the VP1 sequence is of AAV5. A preferred capsid protein is AAV5, preferably as provided in SEQ ID NO: 22 or AAV5, preferably as provided in SEQ ID NO: 28 as listed in Lubelski et al. WO2015137802. Thus, in a preferred embodiment, the AAV capsid proteins are AAV serotype 5 or AAV serotype 8 capsid proteins that have been modified according to the invention. More preferably, the AAV capsid proteins are AAV serotype 5 capsid proteins that have been modified according to the invention. It is understood that the exact molecular weights of the capsid proteins, as well as the exact positions of the translation initiation codons may differ between different parvoviruses. However, the skilled person will know how to identify the corresponding position in nucleotide sequence from other parvoviruses than AAV-5. Alternatively, the sequence encoding AAV capsid proteins is a man-made sequence, for example as a result of directed evolution experiments. This can include generation of capsid libraries via DNA shuffling, error prone PCR, bioinformatic rational design, site saturated mutagenesis. Resulting capsids are based on the existing serotypes but contain various amino acid or nucleotide changes that improve the features of such capsids. The resulting capsids can be a combination of various parts of existing serotypes, "shuffled capsids" or contain completely novel changes, i.e. additions, deletions or substitutions of one or more amino acids or nucleotides, organized in groups or spread over the whole length of gene or protein. See for example Schaffer and Maheshri; Proceedings of the 26th Annual International Conference of the IEEE EMBS San Francisco, Calif., USA; Sep. 1-5, 2004, pages 3520-3523; Asuri et al. (2012) Molecular Therapy 20(2):329-3389; Lisowski et al. (2014) Nature 506(7488):382-386, herein incorporated by reference.

In a preferred embodiment of the invention, the open reading frame encoding VP3 capsid protein starts with non-canonical translation initiation codon selected from the group consisting of: ACG, ATT, ATA, AGA, AGG, AAA, CTG, CTT, CTC, CTA, CGA, CGC, TTG, TAG and GTG. Preferably, the non-canonical translation initiation codon is selected from the group consisting of GTG, CTG, ACG, TTG, more preferably the non-canonical translation initiation codon is CTG.

The nucleotide sequence of the invention for expression of the AAV capsid proteins further preferably comprises at least one modification of the nucleotide sequence encoding AAV VP1 capsid protein selected from among a G at nucleotide position 12, an A at nucleotide position 21, and a C at nucleotide position 24 of the VP1 open reading frame, wherein the nucleotide positions correspond to the nucleotide positions of the wild-type nucleotide sequences. A "potential/possible false start site" or "potential/possible false translation initiation codon" is herein understood to mean an in-frame ATG codon located in the coding sequence of the capsid protein(s). Elimination of possible false start sites for translation within the VP1 coding sequences of other serotypes will be well understood by an artisan of skill in the art, as will be the elimination of putative splice sites that may be recognized in insect cells. For example, the modification of the nucleotide at position 12 is not required for recombinant AAV5, since the nucleotide T is not giving rise to a false ATG codon. The various modifications of the wild-type AAV sequences for proper expression in insect cells is achieved by application of well-known genetic engineering techniques such as described e.g. in Sambrook and Russell (2001) "Molecular Cloning: A Laboratory Manual (3$^{rd}$ edition), Cold Spring Harbor Laboratory, Cold Spring Harbor Laboratory Press, New York. Various further modifications of VP coding regions are known to the skilled artisan which could either increase yield of VP and virion or have other desired effects, such as altered tropism or reduce antigenicity of the virion. These modifications are within the scope of the present invention.

Preferably the nucleotide sequence of the invention encoding the AAV capsid proteins is operably linked to expression control sequences for expression in an insect cell. Thus, in a second aspect, the present invention relates to a nucleic acid construct comprising a nucleic acid molecule according to the invention, wherein the nucleotide sequence of the open reading frame encoding the adeno-associated virus (AAV) capsid proteins is operably linked to expression control sequences for expression in an insect cell. These expression control sequences will at least include a promoter that is active in insect cells. Techniques known to one skilled in the art for expressing foreign genes in insect host cells can be used to practice the invention. Methodology for molecular engineering and expression of polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex.; Luckow. 1991. In Prokop et al., Cloning and Expression of Heterologous Genes in Insect Cells with Baculovirus Vectors' Recombinant DNA Technology and Applications, 97-152; King, L. A. and R. D. Possee, 1992, The baculovirus expression system, Chapman and Hall, United Kingdom; O'Reilly, D. R., L. K. Miller, V. A. Luckow, 1992, Baculovirus Expression Vectors: A Laboratory Manual, New York; W. H. Freeman and Richardson, C. D., 1995, Baculovirus Expression Protocols, Methods in Molecular Biology, volume 39; U.S. Pat. No. 4,745,051; US2003148506; and WO 03/074714. A particularly suitable promoter for transcription of the nucleotide sequence of the invention encoding of the AAV capsid proteins is e.g. the polyhedron promoter (polH), such a polH promoter provided in SEQ ID NO:70 (or as listed as SEQ ID NO:53, and shortened version thereof SEQ ID NO: 54, in Lubelski et al. WO2015137802). However, other promoters that are active in insect cells and that may be selected according to the invention are known in the art, e.g. a polyhedrin (polH) promoter, p10 promoter, p35 promoter, 4×Hsp27 EcRE+minimal Hsp70 promoter, deltaE1 promoter, E1 promoter or IE-1 promoter and further promoters described in the above references. Preferably the nucleic acid construct for expression of the AAV capsid proteins in insect cells is an insect cell-compatible vector. An "insect cell-compatible vector" or "vector" is understood to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In a preferred embodiment, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

In a third aspect, the invention relates to an insect cell comprising a nucleic acid construct of the invention as defined above. Any insect cell which allows for replication of AAV and which can be maintained in culture can be used in accordance with the present invention. For example, the cell line used can be from Spodoptera frugiperda, drosophila cell lines, or mosquito cell lines, e.g., Aedes albopictus derived cell lines. Preferred insect cells or cell lines are cells from the insect species which are susceptible to baculovirus infection, including e.g. expresSF+®, Drosophila Schneider 2 (S2) Cells, Se301, SeIZD2109, SeUCR1, Sf9, Sf900+, Sf21, BTI-TN-5B1-4, MG-1, Tn368, HzAm1, Ha2302, Hz2E5 and High Five from Invitrogen.

A preferred insect cell according to the invention further comprises: (a) a second nucleotide sequence comprising at least one AAV inverted terminal repeat (ITR) nucleotide sequence; (b) a third nucleotide sequence comprising a Rep52 or a Rep40 coding sequence operably linked to expression control sequences for expression in an insect cell; and, (c) a fourth nucleotide sequence comprising a Rep78 or a Rep68 coding sequence operably linked to expression control sequences for expression in an insect cell.

In the context of the invention "at least one AAV ITR nucleotide sequence" is understood to mean a palindromic sequence, comprising mostly complementary, symmetrically arranged sequences also referred to as "A," "B," and "C" regions. The ITR functions as an origin of replication, a site having a "cis" role in replication, i.e., being a recognition site for trans acting replication proteins (e.g., Rep 78 or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. An AAV replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for AAV replication of a circular vector. Thus, one ITR nucleotide sequence can be used in the context of the present invention. Preferably, however, two or another even number of regular ITRs are used. Most preferably, two ITR sequences are used. In view of the safety of viral vectors it may be desirable to construct a viral vector that is unable to further propagate after initial introduction into a cell. Such a safety mechanism for limiting undesirable vector propagation in a recipient may be provided by using rAAV with a chimeric ITR as described in US2003148506. In a preferred embodiment, the nucleotide sequence encoding the parvoviral VP1, VP2 and VP3 capsid proteins comprises at least one in frame insertion of a sequence coding for an immune evasion repeat, such as described in WO 2009/154452. This results in formation of a so-called self-complementary or monomeric duplex parvoviral virion. In a preferred embodiment, the sequence encoding the parvoviral VP1, VP2 and VP3 capsid proteins comprises a monomeric duplex or self-complementary genome. For the preparation of a monomeric duplex AAV vector, AAV Rep proteins and AAV capsid proteins are expressed in insect cells according to the present invention and in the presence of a vector genome comprising at least one AAV ITR, wherein Rep52 and/or Rep40 protein expression is increased relative to Rep78 and/or Rep68 protein expression. Monomeric duplex AAV vectors, can also be prepared by expressing in insect cells AAV Rep proteins and AAV Cap proteins in the presence of a vector genome construct flanked by at least one AAV ITR, wherein the nicking activity of Rep78 and/or Rep 60 is reduced relative to the helicase/encapsidation activity of Rep52 and/or Rep 40, as for example described in WO2011/122950.

The number of vectors or nucleic acid constructs employed is not limiting in the invention. For example, one, two, three, four, five, six, or more vectors can be employed to produce AAV in insect cells in accordance with the present invention. If six vectors are employed, one vector encodes AAV VP 1, another vector encodes AAV VP2, yet another vector encodes AAV VP3, still yet another vector encodes Rep52 or Rep40, while Rep78 or Rep 68 is encoded by another vector and a final vector comprises at least one AAV ITR. Additional vectors might be employed to express, for example, Rep52 and Rep40, and Rep78 and Rep 68. If fewer than six vectors are used, the vectors can comprise various combinations of the at least one AAV ITR and the VP1, VP2, VP3, Rep52/Rep40, and Rep78/Rep68 coding sequences. Preferably, two vectors or three vectors are used, with two vectors being more preferred as described above. If two vectors are used, preferably the insect cell comprises: (a) a first nucleic acid construct for expression of the AAV capsid proteins as defined above, which construct further comprises the third and fourth nucleotide sequences as defined in (b) and (c) above, the third nucleotide sequence comprising a Rep52 or a Rep40 coding sequence operably linked to at least one expression control sequence for expression in an insect cell, and the fourth nucleotide sequence comprising a Rep78 or a Rep68 coding sequence operably linked to at least one expression control sequence for expression in an insect cell; and (b) a second nucleic acid construct comprising the second nucleotide sequence as defined in (a) above, comprising at least one AAV ITR nucleotide sequence. If three vectors are used, preferably the same configuration as used for two vectors is used except that separate vectors are used for expression of the capsid proteins and for expression of the Rep52, Rep40 Rep78 and Rep68 proteins. The sequences on each vector can be in any order relative to each other. For example, if one vector comprises ITRs and an ORF comprising nucleotide sequences encoding VP capsid proteins, the VP ORF can be located on the vector such that, upon replication of the DNA between ITR sequences, the VP ORF is replicated or not replicated. For another example, the Rep coding sequences and/or the ORF comprising nucleotide sequences encoding VP capsid proteins can be in any order on a vector. In is understood that also the second, third and further nucleic acid construct(s) preferably are an insect cell-compatible vectors, preferably a baculoviral vectors as described above. Alternatively, in the insect cell of the invention, one or more of the first nucleotide sequence, second nucleotide sequence, third nucleotide sequence, and fourth nucleotide sequence and optional further nucleotide sequences may be stably integrated in the genome of the insect cell. One of ordinary skill in the art knows how to stably introduce a nucleotide sequence into the insect genome and how to identify a cell having such a nucleotide sequence in the genome. The incorporation into the genome may be aided by, for example, the use of a vector comprising nucleotide sequences highly homologous to regions of the insect genome. The use of specific sequences, such as transposons, is another way to introduce a nucleotide sequence into a genome.

Thus, in a preferred embodiment, an insect cell according to the invention comprises: (a) a first nucleic acid construct according to the invention, whereby the first nucleic acid construct further comprises the third and fourth nucleotide sequences as defined above; and, (b) a second nucleic acid construct comprising the second nucleotide sequence as defined above, wherein the second nucleic acid construct preferably is an insect cell-compatible vector, more preferably a baculoviral vector.

In a preferred embodiment of the invention, the second nucleotide sequence present in the insect cells of the invention, i.e. the sequence comprising at least one AAV ITR, further comprises at least one nucleotide sequence encoding a gene product of interest (preferably for expression in a mammalian cell), whereby preferably the at least one nucleotide sequence encoding a gene product of interest becomes incorporated into the genome of an AAV produced in the insect cell. Preferably, at least one nucleotide sequence encoding a gene product of interest is a sequence for expression in a mammalian cell. Preferably, the second nucleotide sequence comprises two AAV ITR nucleotide sequences and wherein the at least one nucleotide sequence encoding a gene product of interest is located between the two AAV ITR nucleotide sequences. Preferably, the nucleotide sequence encoding a gene product of interest (for expression in the mammalian cell) will be incorporated into the AAV genome produced in the insect cell if it is located between two regular ITRs, or is located on either side of an ITR engineered with two D regions. Thus, in a preferred embodiment, the invention provides an insect cell according the invention, wherein the second nucleotide sequence comprises two AAV ITR nucleotide sequences and wherein the at least one nucleotide sequence encoding a gene product of interest is located between the two AAV ITR nucleotide sequences.

Typically, the gene product of interest, including ITRs, is 5,000 nucleotides (nt) or less in length. In another embodiment, an oversize DNA, i.e. more than 5,000 nt in length, can be expressed in vitro or in vivo by using AAV vector described by the present invention. An oversized DNA is here understood as a DNA exceeding the maximum AAV packaging limit of 5 kbp. Therefore, the generation of AAV vectors able to produce recombinant proteins that are usually encoded by larger genomes than 5.0 kb is also feasible. For instance, the present inventors have generated rAAV5 vectors containing partial, uni-directionally packaged fragments of hFVIII in insect cells. The total size of vector genome encompassing at least 5.6 kb packaged into two populations of FVIII fragment-containing AAV5 particles. These variant AAV5-FVIII vectors were shown to drive expression and secretion of active FVIII. This was confirmed in vitro, where the AAV vector comprising a gene product of interest encoding Factor VIII after infection of Huh7 cells resulted in production of active FVIII protein. Similarly, tail vein delivery of rAAV.FVIII in mice resulted in production of active FVIII protein. The molecular analysis of the encapsidation products unequivocally showed that the 5.6 kbp FVIII expression cassette is not entirely encapsidated in AAV particle. Without wishing to be bound by any theory, we hypothesize that + and − DNA strands of the encapsidated molecules revealed missing 5' ends. This is consistent with a previously reported unidirectional (starting at 3' end) packaging mechanism operating according to "head-full principia" with 4.7-4.9 kbp limit (see for example Wu et al. [2010] Molecular Therapy 18(1):80-86; Dong et al. [2010] Molecular Therapy 18(1):87-92; Kapranov et al. [2012] Human Gene Therapy 23:46-55; and in particular Lai et al. [2010] Molecular Therapy 18(1):75-79. Although only approximately 5 kb of the whole 5.6 kb vector genome was encapsidated, the vector was potent and lead to expression of active FVIII. We have shown that the correct template for production of FVIII was assembled in the target cell based on partial complementation of + and – DNA strains followed by second strand synthesis.

The second nucleotide sequence defined herein above may thus comprise a nucleotide sequence encoding at least one "gene product of interest" for expression in a mammalian cell, located such that it will be incorporated into an AAV genome replicated in the insect cell. Any nucleotide sequence can be incorporated for later expression in a mammalian cell transfected with the AAV produced in accordance with the present invention, as long as the constructs remain within the packaging capacity of the AAV virion. The nucleotide sequence may e.g. encode a protein it may express an RNAi agent, i.e. an RNA molecule that is capable of RNA interference such as e.g. a shRNA (short hairpin RNA) or an siRNA (short interfering RNA). "siRNA" means a small interfering RNA that is a short-length double-stranded RNA that are not toxic in mammalian cells (Elbashir et al., 2001, Nature 411: 494-98; Caplen et al., 2001, Proc. Natl. Acad. Sci. USA 98: 9742-47). In a preferred embodiment, the second nucleotide sequence may comprise two nucleotide sequences and each encodes one gene product of interest for expression in a mammalian cell. Each of the two nucleotide sequences encoding a product of interest is located such that it will be incorporated into a rAAV genome replicated in the insect cell.

The product of interest for expression in a mammalian cell may be a therapeutic gene product. A therapeutic gene product can be a polypeptide, or an RNA molecule (siRNA), or other gene product that, when expressed in a target cell, provides a desired therapeutic effect such as e.g. ablation of an undesired activity, e.g. the ablation of an infected cell, or the complementation of a genetic defect, e.g. causing a deficiency in an enzymatic activity. Examples of therapeutic polypeptide gene products include CFTR, Factor IX, Lipoprotein lipase (LPL, preferably LPL S447X; see WO 01/00220), Apolipoprotein A1, Uridine Diphosphate Glucuronosyltransferase (UGT), Retinitis Pigmentosa GTPase Regulator Interacting Protein (RP-GRIP), cytokines or interleukins like e.g. IL-10, dystrophin, PBGD, NaGLU, Treg167, Treg289, EPO, IGF, IFN, GDNF, FOXP3, Factor VIII, VEGF, AGXT and insulin. Alternatively, or in addition as a second gene product, second nucleotide sequence defined herein above may comprise a nucleotide sequence encoding a polypeptide that serve as marker proteins to assess cell transformation and expression. Suitable marker proteins for this purpose are e.g. the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel (2001) "Molecular Cloning: A Laboratory Manual (3$^{rd}$ edition), Cold Spring Harbor Laboratory, Cold Spring Harbor Laboratory Press, New York. Furthermore, second nucleotide sequence defined herein above may comprise a nucleotide sequence encoding a polypeptide that may serve as a fail-safe mechanism that allows to cure a subject from cells transduced with the rAAV of the invention, if deemed necessary. Such a nucleotide sequence, often referred to as a suicide gene, encodes a protein that is capable of converting a prodrug into a toxic substance that is capable of killing the transgenic cells in which the protein is expressed. Suitable examples of such suicide genes include e.g. the *E. coli* cytosine deaminase gene or one of the thymidine kinase genes from Herpes Simplex Virus, Cytomegalovirus and Varicella-Zoster virus, in which case ganciclovir may be used as prodrug to kill the transgenic cells in the subject (see e.g. Clair et al., 1987, Antimicrob. Agents Chemother. 31: 844-849).

In another embodiment, the gene product of interest can be an AAV protein. In particular, a Rep protein, such as Rep78 or Rep68, or a functional fragment thereof. A nucleotide sequence encoding a Rep78 and/or a Rep68, if present on the rAAV genome of the invention and expressed in a mammalian cell transduced with the rAAV of the invention, allows for integration of the rAAV into the genome of the transduced mammalian cell. Expression of Rep78 and/or Rep68 in an rAAV-transduced or infected mammalian cell can provide an advantage for certain uses of the rAAV, by allowing long term or permanent expression of any other gene product of interest introduced in the cell by the rAAV.

In the rAAV vectors of the invention the at least one nucleotide sequence(s) encoding a gene product of interest for expression in a mammalian cell, preferably is/are operably linked to at least one mammalian cell-compatible expression control sequence, e.g., a promoter. Many such promoters are known in the art (see Sambrook and Russel, 2001, supra). Constitutive promoters that are broadly expressed in many cell-types, such as the CMV promoter may be used. However, more preferred will be promoters that are inducible, tissue-specific, cell-type-specific, or cell cycle-specific. For example, for liver-specific expression a promoter may be selected from an a1-anti-trypsin promoter, a thyroid hormone-binding globulin promoter, an albumin promoter, LPS (thyroxine-binding globin) promoter, HCR-ApoCII hybrid promoter, HCR-hAAT hybrid promoter and an apolipoprotein E promoter, LP1, HLP, minimal TTR promoter, FVIII promoter, hyperon enhancer, ealb-hAAT. Other examples include the E2F promoter for tumor-selective, and, in particular, neurological cell tumor-selective expression (Parr et al., 1997, Nat. Med. 3:1145-9) or the IL-2 promoter for use in mononuclear blood cells (Hagenbaugh et al., 1997, J Exp Med; 185: 2101-10).

AAV is able to infect a number of mammalian cells. See, e.g., Tratschin et al., Mol. Cell Biol., 5(11):3251-3260 (1985) and Grimm et al., Hum. Gene Ther., 10(15):2445-2450 (1999). However, AAV transduction of human synovial fibroblasts is significantly more efficient than in similar murine cells, Jennings et al., Arthritis Res, 3:1 (2001), and the cellular tropicity of AAV differs among serotypes. See, e.g., Davidson et al., Proc. Natl. Acad. Sci. USA, 97(7): 3428-3432 (2000) (discussing differences among AAV2, AAV4, and AAV5 with respect to mammalian CNS cell tropism and transduction efficiency).

As said, AAV sequences that may be used in the present invention for the production of AAV in insect cells can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901; GenBank Accession number AF043303; GenBank Accession number AF085716; Chlorini et al. (1997, J. Vir. 71: 6823-33); Srivastava et al. (1983, J. Vir. 45:555-64); Chlorini et al. (1999, J. Vir. 73:1309-1319); Rutledge et al. (1998, J. Vir. 72:309-319); and Wu et al. (2000, J. Vir. 74: 8635-47). Human or simian adeno-associated virus (AAV) serotypes are preferred sources of AAV nucleotide sequences for use in the context of the present invention, more preferably AAV serotypes which normally infects humans (e.g., serotypes 1, 2, 3A, 3B, 4, 5, 6, 7, 8, 9, 10, 11, 12 and 13) or primates (e.g., serotypes 1 and 4).

Preferably the AAV ITR sequences for use in the context of the present invention are derived from AAV1, AAV2, AAV5 and/or AAV4. Likewise, the Rep52, Rep40, Rep78 and/or Rep68 coding sequences are preferably derived from AAV1, AAV2, and/or AAV4. The sequences coding for the VP1, VP2, and VP3 capsid proteins for use in the context of the present invention may be taken from any of the known 42 serotypes, more preferably from AAV1, AAV2, AAV3, AAV4, AAV5, AAV6, AAV7, AAV8 or AAV5 or newly developed AAV-like particles obtained by e.g. capsid shuffling techniques and AAV capsid libraries. In a preferred embodiment, the sequences coding for the VP1, VP2, and VP3 capsid proteins are from AAV5 or AAV8, more preferably from AAV5.

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82% (Bantel-Schaal et al., 1999, J. Virol., 73(2):939-947). Moreover, the Rep sequences and ITRs of many AAV serotypes are known to efficiently cross-complement (i.e., functionally substitute) corresponding sequences from other serotypes in production of AAV particles in mammalian cells. US2003148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability Rep and ITR sequences to cross-complement corresponding sequences of other serotypes allows for the production of pseudotyped AAV particles comprising the capsid proteins of a serotype (e.g., AAV3) and the Rep and/or ITR sequences of another AAV serotype (e.g., AAV2). Such pseudotyped AAV particles are a part of the present invention.

As said, modified "AAV" sequences also can be used in the context of the present invention, e.g. for the production of rAAV vectors in insect cells. Such modified sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV5 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. In view thereof, the production of AAV5 can differ from production of other serotypes in insect cells. Where methods of the invention are employed produce rAAV5, it is preferred that one or more vectors comprising, collectively in the case of more than one vector, a nucleotide sequence comprising an AAV5 ITR, a nucleotide sequence comprises an AAV5 Rep52 and/or Rep40 coding sequence, and a nucleotide sequence comprises an AAV5 Rep78 and/or Rep68 coding sequence. Such ITR and Rep sequences can be modified as desired to obtain efficient production of rAAV5 or pseudotyped rAAV5 vectors in insect cells. E.g., the start codon of the Rep sequences can be modified.

In a preferred embodiment, the first nucleotide sequence, second nucleotide sequence, third nucleotide sequence and optionally fourth nucleotide sequence are stably integrated in the genome of the insect cell.

A preferred AAV according to the invention is a virion comprising in its genome at least one nucleotide sequence encoding a gene product of interest, whereby the at least one nucleotide sequence preferably is not a native AAV nucleotide sequence, and whereby the AAV virion comprises a VP1 capsid protein that comprises a methionine at amino acid position 1 and a valine at position 2. Even more preferred is an AAV virion that is obtainable from an insect cell as defined above in e.g. a method as defined herein below.

An advantage of the AAV virions of the invention is their improved infectivity. Without wishing to be bound by any theory, it seems that the infectivity increases with an increase of the amount of VP1 protein in the capsid in relation to the amounts of VP2 and/or VP3 in the capsid combined with the valine at position 2 of VP1. The infectivity of an AAV virion is herein understood to mean the efficiency of transduction of the transgene comprised in the virion, as may be deduced from the expression rate of the transgene and the amount or activity of the product expressed from the transgene.

Preferably, an AAV virion of the invention comprises a gene product of interest that encodes a polypeptide gene product selected from the group consisting of: CFTR, Factor IX, Lipoprotein lipase (LPL, preferably LPL S447X; see WO 01/00220), Apolipoprotein A1, Uridine Diphosphate Glucuronosyltransferase (UGT), Retinitis Pigmentosa GTPase Regulator Interacting Protein (RP-GRIP), cytokines or interleukins like e.g. IL-10, dystrophin, PBGD, NaGLU, Treg167, Treg289, EPO, IGF, IFN, GDNF, FOXP3, Factor VIII, VEGF, AGXT and insulin. More preferably, the gene product of interest encodes a Factor IX or a Factor VIII protein.

In another aspect, the invention thus relates to a method for producing an AAV in an insect cell. Preferably the method comprises the steps of: (a) culturing an insect cell as defined in herein above under conditions such that AAV is produced; and, optionally, (b) recovery of the AAV. Growing conditions for insect cells in culture, and production of heterologous products in insect cells in culture are well-known in the art and described e.g. in the above cited references on molecular engineering of insect cells.

Preferably the method further comprises the step of affinity-purification of the AAV using an anti-AAV antibody, preferably an immobilized antibody. The anti-AAV antibody preferably is an monoclonal antibody. A particularly suitable antibody is a single chain camelid antibody or a fragment thereof as e.g. obtainable from camels or llamas (see e.g. Muyldermans, 2001, Biotechnol. 74: 277-302). The antibody for affinity-purification of AAV preferably is an antibody that specifically binds an epitope on a AAV capsid protein, whereby preferably the epitope is an epitope that is present on capsid protein of more than one AAV serotype. E.g. the antibody may be raised or selected on the basis of specific binding to AAV2 capsid but at the same time also it may also specifically bind to AAV1, AAV3 and AAV5 capsids.

In another aspect of the invention, a method is provided for providing a nucleic acid construct encoding a parvoviral capsid protein, said nucleic acid construct having one or more improved properties, which method comprises:
a) providing a plurality of nucleic acid constructs, each construct comprising:
a nucleotide sequence encoding a parvoviral capsid protein operably linked to an expression control sequence and at least one parvoviral inverted terminal repeat (ITR) sequence flanking said nucleotide sequence encoding a parvoviral capsid protein operably linked to an expression control sequence;
b) transferring the plurality of nucleic acid constructs into insect cells which are capable of expressing parvoviral Rep protein;
c) subjecting the insect cells to conditions to allow for expression of parvoviral capsid protein and the parvoviral rep protein so that the nucleic acid constructs can be packaged into parvoviral capsids to provide for parvoviral virions;
d) recovering parvoviral virions from the insect cells and/or insect cell supernatant;
e) contacting said parvoviral virions with a target cell to allow for infection of the target cell;
f) recovering or identifying the nucleic acid constructs from the target cells.

As shown in the example section and as described above, this method is in particular useful for selecting first of all nucleic acid constructs that are highly functional in insect cells, in the sense that the constructs are capable of producing good amounts of capsids containing a vector genome, but also capable of generating constructs contained capsids that are highly effective in transferring, and subsequently express, its DNA to a target cell.

It is understood that with regard to a plurality of nucleic acid constructs is meant constructs that vary with regard to expression control sequences and/or the nucleic acid sequence encoding the amino acid sequence of the capsid protein and/or the amino acid sequence of the capsid protein and/or the ITR sequence(s). Hence, any variation therein can be contemplated. With regard to any improvement of properties, these can be in relation to a reference sequence, e.g. a wild-type sequence or a nucleic acid construct of the prior art for the production of AAV capsid in insect cells. Any property that may need improvement can be contemplated which relates to the sequences that can be varied in the plurality of nucleic acid constructs. Such properties may include, but are not limited to, for example improved potency, improved yield, improved target cell selectivity.

Creating molecular diversity or mutagenesis is the first step in the method of the invention. By introducing random point mutations in a reference sequence for which improvement is sought, via an error prone (EP) PCR for example, a plurality of nucleic acids encoding mutant sequences (i.e. a library of mutant nucleic acids). As said, said random mutations may be contained in non-encoding sequences and/or coding sequences. The frequencies of mutations that can be introduced may be changed by varying the amount of template and PCR cycles, and the mutagenic primers used. It is understood that when reference is made to plurality, this involves 100 or more, preferably 1,000 or more, 10,000 or more, 100,000 or more, or 1000,0000 or more different sequences, depending on the variation that is to be introduced in the plurality of nucleic acid constructs. It is understood that the terms "library" or "plurality" can have the same meaning herein in the sense that they refer to a large number of different sequences that can e.g. be related, i.e. have substantial sequence identity. Each member of the library, i.e. each different sequence, may be represented more than 1 time in the library. For example, when a library contains 1000 unique sequences, the library may contain 1000,000 sequences altogether. This means that on average of each library member 1000 copies are present in the library.

Mutagenesis may be carried out in any manner known to the skilled person. For example, such mutagenesis could be random, although such mutagenesis could be directed (i.e. for example, to target specific sequences/structures within a nucleic acid construct). Random mutagenesis may be carried out to achieve low mutation rates, for example to provide sequences which encode a Cap protein having one, two, three, four, five, six, seven, eight, nine or ten or more amino acid changes (as compared with the starting sequence on which mutagenesis is carried out).

Techniques which may be used to carry out random mutagenesis include *E. coli* XL1red, UV irradiation, chemical methods (for example deamination, alkylation or base-analog mutagens) or PCR methods (for example DNA shuffling, site-directed random mutagenesis or error prone PCR).

Error prone PCR is a modification of standard PCR protocols, designed to alter and enhance the natural error rate of the polymerase. Taq polymerase may be used because of its naturally high error rate, with errors biased toward AT to GC changes. However, it is also possible to use alternative forms of polymerase whose biases allow for increased variation in mutation type (i.e. more GC to AT changes).

Error-prone PCR reactions typically contain higher concentrations of $MgCl_2$ compared to basic PCR reactions, in order to stabilize non-complementary pairs. $MgCl_2$ can also be added to increase the error-rate. Other ways of modifying mutation rates include varying the rations of nucleotides in the reaction, or including a nucleotide analog such as 8-oxo-GTP or dITP. Mutation rates may also be modified by changing the number of effective doublings by increasing/decreasing the number of cycles or by changing the initial template concentration.

In any case, whichever way the mutations are introduced, the resulting plurality of sequences are subsequently cloned into a nucleic acid construct to obtain a plurality of nucleic acid constructs. Said nucleic acid construct contains one or more parvoviral or AAV ITRs flanking a nucleotide sequence encoding a parvoviral capsid protein operably linked to an expression control sequence (typically flanked by two AAV ITRs). Said nucleic acid construct may also contain e.g. in between the ITR optionally a reporter gene expression cassette, such as a green fluorescent protein (GFP) expression cassette, under the control of a promoter, such as the CMV and the baculovirus p10 promoter. The plurality of constructs can subsequently be introduced in a destination vector, e.g. a baculovirus vector to obtain a library of baculoviruses. This can be easily achieved by using common biomolecular techniques such as homologous recombination and also by using commercially available systems like Bac-to-Bac. Each baculovirus in the library containing a single nucleic acid construct, wherein the single nucleic acid constructs have the intended sequence variation. The complexity of the library is preferably maintained when the baculovirus library is generated (i.e. the amount of unique sequences in the baculovirus library stays about the same when compared with the nucleic acid library). Hence, preferably, the nucleic acid constructs as defined in step a) of the method above are contained in baculovirus vectors.

Subsequently, the plurality of constructs is transferred to insect cells. Preferably, a plurality of baculoviruses is used. This is because with baculoviruses the multiplicity of infection can be well controlled. Hence, when a baculovirus library is used the multiplicity of infection is preferably kept below 1, preferably below 0.5, more preferably below 0.1. For example, with an moi of 0.5, the majority of insect cells will have a single baculovirus per cell, however, a significant portion of these cells will have two baculoviruses from the library per cell, and most cells will not be infected. The number of baculoviruses per cell being governed by Poisson distribution. Lowering the moi reduces the number of cells having more than 1 baculovirus even further. It may however not be necessary according to the invention to know the multiplicity of infection. For example, as shown in the example section a dilution serious of the plurality of baculoviruses can also be used and the dilution that provides optimal AAV vector library production (e.g. highest titer and/or least cross-packaging) may be selected.

The said insect cells to which the plurality of constructs is provided, also are capable of expressing parvoviral Rep protein. For example, an additional baculovirus containing a Rep expression construct may be used to transfer a Rep expression construct to the cells. Preferably, a relatively high multiplicity of infection is used such that Rep is not a limiting factor, i.e. when a cell is provided with one of the plurality of constructs, the chance is great that the cell will also have a Rep expression construct. Alternatively, a stable cell line may also be used that contains the Rep expression construct, which can constitutively express Rep protein or may inducible express Rep when one of the plurality of constructs is transferred to the cells. In any case, the said insect cells that are capable of expressing parvoviral Rep protein and which are provided with one (or more) of the plurality of constructs according to the invention is next subjected to conditions to allow for expression of parvoviral capsid protein and the parvoviral rep protein so that the nucleic acid constructs can be packaged into parvoviral capsids to provide for parvoviral virions. Mostly this involves culturing the cells for some time when e.g. the baculovirus system is used. Preferably, when the baculovirus vector system is used, conditions are selected that do not allow spreading of the baculoviruses to such an extent that many if not most cells will contain several members of the construct library. Conditions are preferably selected such that the majority of cells that contain a construct from the library will contain a single construct and will produce only the parvoviral capsid encoded by said construct which also contains said single construct. When conditions would be selected in which more than one construct would be contained in an insect cell, wherein one of the constructs produces infectious or potent AAV, the constructs that are much less potent or not infectious would be cross-packaged which makes it difficult to determine which construct of all packaged constructs is capable of producing potent AAV. In other words, having low cross-packaging allows for a more stringent and more effective selection.

Next, the parvovirus virions are recovered from the insect cells and/or insect cell supernatant. Numerous methods for recovery of parvoviral virions are available and include method such as described in the example section. Also, conventional methods such as density (step) gradient centrifugation may be used (iodixanol, CsCl), and/or tangential flow filtration. Such conventional methods may be useful when for example in capsid sequences variations are introduced that could have an effect on affinity chromatography. Nevertheless, it may also be contemplated to include a specific affinity chromatography step as one of the features based on which constructs may be selected. Hence, improved specific affinity chromatography features may be one of the features that may be contemplated to improve as well. Nevertheless, efficient production in insect cells and infectivity or potency remain features which need either to remain and/or which can be improved.

In another embodiment, a parvoviral virion library produced by the methods as described above is provided. In a further embodiment, a parvoviral library comprising a variety of parvoviral vectors, is provided, said parvoviral vector library comprising parvoviral vector capsids wherein each parvoviral capsid contains a parvoviral vector genome that comprises an expression cassettes for expression of parvoviral capsid proteins. Preferably, said parvoviral vector library comprising a variety of parvoviral vectors comprises parvoviral vector capsids, wherein each parvoviral capsid contains a parvoviral vector genome that comprises an expression cassettes for expression of parvoviral capsid proteins in insect cells. More preferably, said parvoviral vector library comprising a variety of parvoviral vectors comprises parvoviral vector capsids, wherein of substantially each parvoviral capsid contained in the library, a parvoviral capsid contains a parvoviral vector genome that comprises an expression cassettes for expression in insect cells of the parvoviral capsid proteins it is encapsidated in. Alternatively, as said, the vector genome may not necessarily contain the expression cassette, but may also contain a sequence identifier by which the parvovirus amino acid sequence (and/or expression cassette encoding it) in which the vector genome is encapsidated may be identified (see FIGS. 6A-6C). In other words, the library contains substantially parvoviral capsids which may contain any sequence within the vector genome encapsidated, as long as from the sequence contained within the vector genome the corresponding parvoviral capsid (i.e. the amino acid sequence thereof) in which it is contained can be identified.

Specific identifier sequences (see FIG. 6B) that may be contemplated are preferably at least 10, 11, 12, 13, 14, 15, 16, 17, 18, 19, or 20 nucleotides in length. Specific identifier sequences that may be contemplated may be at most 50, 60, 70, 80, or 90 nucleotides in length. With an identifier sequence of at least 15 nucleotides, about 10e9 possible unique combinations are possible. Having longer sequence identifiers may allow for more redundancy and a more reliable identification. It is understood that a sequence identifier may be a priori coupled to a specific capsid sequence. Hence, when in such a scenario the sequence identifier is sequenced or detected, one may by reference to a table identify the corresponding capsid expression cassette. Alternatively, one may use the sequence identifier by capturing and/or sequencing the vector vehicle genome such as the baculovirus genome such that the capsid expression cassette sequence or part thereof can be determined that is associated with a sequence identifier. Such analysis and/or sequence determination may be done afterwards. Such means and methods for sequence determination using high through put technologies to identify sequences from complex libraries are well known in the art.

The libraries according to the invention as described above or produced as described above may be provided as a crude lysate or purified product. In particular, such libraries may preferably be produced from a virus vector that contains the vector genome and encodes the parvovirus capsid protein. A preferred vector used to generate the library may be a baculovirus vector containing expression cassettes for said parvoviral capsid protein that are active in insect cells. Alternatively, one can easily envisage any alternative suitable virus vector library and cell line may be contemplated, such as e.g. an Adenoviral, HSV, lentiviral vector based system may be used instead of baculovirus, wherein the expression cassette for the capsid protein is suitable for (or is to be selected therefor) expression in mammalian cells such as e.g. HeLa cells, 293 cells, CHO cells, A549, 293T, COS. Such alternative vector vehicles and suitable cell lines that may be contemplated are well known in the art as e.g. described in the $4^{th}$ edition of Gene and Cell Therapy—Therapeutic Mechanisms and strategies, edited by Nancy Smith Templeton, 2015, CRC Press. Hence, in an alternative embodiment, instead of using baculovirus vectors and insect cells, one may easily use the means and methods as described herein for mammalian cells combined with suitable mammalian virus vehicles. In any case, because the parvovirus vector libraries provided in accordance with the invention, such as AAV libraries, are generated using a vector vehicle that allows control of copy number per producer cell, the quality of the vector library is significantly improved as compared with plasmid produced libraries that do not allow such control.

Next, the parvoviral virions are recovered, or phrased differently, the parvoviral vector library is provided, which may be a crude lysate or purified product, the parvoviral virions thereof are subsequently brought in contact with a selected target cell to allow the parvoviruses to infect the target cells. Suitable target cells may be selected that may be a suitable target cell such as liver cells, kidney cells, neurons for which a gene therapy is being developed. Suitable target cells may be either cell lines, such as for example HeLa cells, HEK293 cells or HuH cells, or may be primary cells. One may even envision that this includes delivery to a suitable animal model, e.g. a rat, a mouse, a monkey, and also may include various delivery routes, e.g. intravenous or intramuscular injections, and that the subsequent target cells are a selected candidate organ in such animal model. In any case, any cell type may be selected and parvovirus virions can be brought into contact therewith in any way, i.e. in vivo or in vitro, to allow for infection, i.e. the transfer of the nucleic acid construct that is contained within capsid virions to the cells. It is understood that cells may also be e.g. co-infected with Adenovirus to aid in the transduction process, e.g. to induce transduction. That may be helpful when e.g. a reporter gene construct is contained within the nucleic acid construct and one wishes to select for cells that allow not only for efficient transfer of the DNA, but also allow for efficient trafficking inside the cell to deliver the nucleic acid constructs to the nucleus (see FIGS. 6A-6C). Without being bound by theory, when capsid sequences are mutated and/or stoichiometry of VP1, VP2 and VP3 changed, this may lead to hampered internal trafficking. For example, capsids lacking VP1 can infect cells, but do not enter the nucleus. The capsids, containing nucleic acid constructs, than remain in the endosome and are targeted for proteolysis by the proteasome. Hence, it may be of interest to include a selection step based on the purpose of the selection process, i.e. to achieve efficient delivery of the nucleic acid construct to the nucleus to allow for expression from the nucleic acid construct. This may be e.g. via a reporter gene or any other gene of interest. This may also be an HeLa RC32 cells, or the like, wherein virions that achieve efficient delivery of the vector genome are amplified.

Lastly, when the cells have been allowed to infect the target cells, preferably to allow for efficient transduction, the nucleic acid constructs are recovered from the target cells. One may recover nucleic acid constructs from the whole cell population. One may also recover nucleic acid constructs from a subset of the cell population, e.g. the subset that shows reporter transgene expression and was thus effective in transducing the target cell. One may also recover nucleic acid constructs from the whole cell population but in particular from the nuclei from the whole cells. This way one may select for nucleic acid constructs (and concomitantly the capsids it encodes as well) that are expected to be good at transducing the target cells. The recovered nucleic acid constructs may next be subjected to sequencing to identify the nucleic acid constructs. As said, the nucleic acid constructs may contain an identifier sequence to identify constructs. It is also understood that when e.g. the baculovirus vector system and insect cells has been used for parvovirus vector library generation, and the parvovirus vector genome contains the expression cassette for the parvovirus capsid in which it is contained, said expression cassette, or part thereof, may be regarded to be an identifier sequence. Said expression cassette when introduced in a mammalian cells may not produce an AAV capsid when it has an insect cell promoter and not a promoter active in mammalian cells. In particular, the part of the nucleic acid construct in which the variation was introduced (or the corresponding identifier sequence) may be subjected to sequencing, e.g. after a PCR reaction wherein the subsection was briefly amplified. One may also sequence the entire nucleic acid construct or the entire capsid encoding sequence. It is understood that sequencing includes high throughput sequencing or any other suitable sequence method known in the art.

Of particular interest may be to identify the improved sequences. When the conditions are selected such that these are highly restrictive, all recovered nucleic acid constructs and the sequences thereof are improved nucleic acid constructs. Hence the recovery of the nucleic acid constructs includes the selection of the improved nucleic acid constructs. Nevertheless, one may confirm or identify improved sequences derived from the recovered nucleic acid constructs by comparing the population of sequences recovered with e.g. population of sequences contained in the library as initially constructed. Recovered sequences that are highly dominant in the recovered population when compared with the initial population being indicative of being the desired improved nucleic acid constructs. Hence, in addition to the recovery of nucleic acid constructs, an additional step may include the identification of the nucleic acid constructs from the library that correspond to improved nucleic acid constructs. Such identification may include a comparison with population sequences of one or more from e.g. the initial library, the baculovirus library containing nucleic acid constructs, the nucleic acid construct population contained in parvovirus capsids.

Once a nucleic acid construct is provided or identified that has the improved properties for which it was selected, the next step is step g), to generate a nucleic acid construct for production of a gene therapy vector comprising a nucleotide sequence encoding a parvoviral capsid protein operably linked to an expression control sequence as recovered in step f). A nucleic acid construct for production of a gene therapy vector does not have an expression construct for parvoviral capsid protein flanked by parvoviral ITR sequences. Hence, the nucleic acid construct for production of a gene therapy vector preferably contains an expression construct for parvoviral capsid protein, and may optionally contain further parvoviral constituents, such as e.g. a gene therapy construct, i.e. a therapeutic gene flanked by parvoviral ITRs, and/or Rep expression constructs, all constructs being constructed for compatibility with insect cells production. Hence, preferably, said generated nucleic acid construct is comprised in a baculovirus vector or an insect cell. As AAV viral vectors are good candidates for gene therapy, in particular the said parvoviral capsid protein, parvoviral Rep protein and/or ITR nucleotide sequences are preferably derived from Adeno-Associated Virus. It is understood that the recovered nucleic acid construct that is used to generate the nucleic acid construct for production of a gene therapy vector may be the actual physical nucleic acid, e.g. as obtained by excising from the recovered nucleic acid construct the sequence of interest. Alternatively, the sequence of interest, e.g. a parvoviral capsid expression cassette or part thereof may be amplified via a PCR reaction and subsequently used. Also, the sequence may be determined and the sequence of interest may be generated de novo, e.g. by a DNA synthesizer.

As the whole selection process is for identifying improved constructs for insect cell based manufacturing of gene therapy vectors for use in a medical treatment, in a further embodiment a method is provided for production of a parvoviral vector comprising the steps a)-g) as described above, wherein an insect cell is provided with
  said generated nucleic acid construct for production of a gene therapy vector
  a nucleic acid construct containing a nucleotide sequence comprising at least one inverted terminal repeat (ITR) nucleotide sequence; and
  a nucleic acid construct encoding parvoviral Rep protein capable of expressing parvoviral Rep protein in an insect cell;
wherein the insect cell is cultured under conditions such that the parvovirus vector is produced; and optionally (b) recovery of the produced parvovirus vector. Preferably said parvoviral vector is an AAV vector. Hence, any of the methods as described above for the production of an AAV vector with a VP1, VP2 and VP3 expression construct having an out of frame initiation codon before the VP1 ATG codon, apply to any identified improved construct and generated nucleic acid construct for production of a gene therapy vector as well.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

1. Introduction

Expression of the AAV capsid in the Baculovirus expression system (BEVS) requires the modification of the expression cassette in order to facilitate a single mRNA transcript to result in the three viral capsid proteins to be produced in the right ratio. Work done by Urabe et al (2002; supra) demonstrated that the adaptation of the start codon combined with the removal of an intron splicing site resulted in the expression of all three VP proteins in insect cells. Further work indicated CTG and GTG can be used as efficient start codons for the production of AAV in the BEVS system. Concomitantly, the an alanine in the second position, e.g. by introduction thereof in an AAV5 capsid sequence, resulted in an AAV5 capsid with native VP1 to VP3 capsid protein ratio's.

Figure 1:
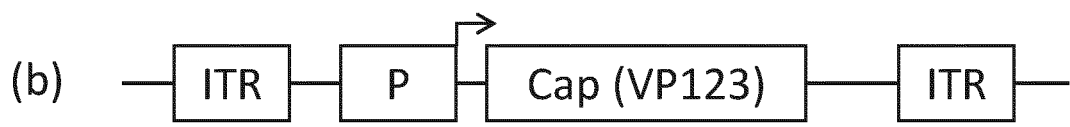
FIG. 1: Schematic representation of library generation and selection process. (a) First, a DNA library is provided. In this particular example, a library of expression constructs having a variety of start codons (XXX) for AAV5 VP1 and having random nucleotides at selected positions (N) (SEQ ID NO:71), examples of such constructs are listed (1 is SEQ ID NO:1; 2 is SEQ ID NO:63; n is SEQ ID NO:65); (b) the DNA library is transferred into vector constructs having expression cassettes with a promoter (P) for expression of capsid proteins of AAV5 VP1, VP2 and VP3 (Cap (VP123)), said expression cassettes flanked by two AAV inverted terminal repeats (ITR) to allow for encapsidation in an AAV capsid. Also, expression cassette(s) for Rep52 and Rep78 are provided; (c) Said Cap and Rep constructs are subsequently transferred to insect cells, in this instance Sf9 cells. Said transfer can be via a baculovirus vector which allows to control for multiplicity of infection; (d) Hence, in the insect cell, the Rep52 and Rep78 proteins that are expressed replicate and encapsidate the AAV vector genomes containing the capsid expression cassettes. As said, when a baculovirus vector is used, the multiplicity of infection can be well controlled and preferably this is kept well below 1 for the Cap construct to have on average only one library member per 519 cell to avoid cross packaging. Only the Cap expression cassettes that effectively produce capsids will encapsidate vector genomes; (e) Next, the capsids containing the vector genomes are tested for infectivity, i.e. efficient transfer of the vector genome to a target cell. A vector particle with a vector genome can be for instance non-infectious, while a vector particle with a vector genome and a VP1:VP2:VP3 ratio of about 1:1:10 is highly infectious. In this example the HeLaRC32 cell line is used which is also capable of replicating AAV vector genomes. From the target cells the vector genomes can be subsequently identified. For example, the vector genome sequence can be determined or the part thereof that contains the varied sequence as shown in (a). Alternatively, an identifier sequence can be determined to identify the library members of (a) that have underwent a successful infection of the target cell.
Figure 1:
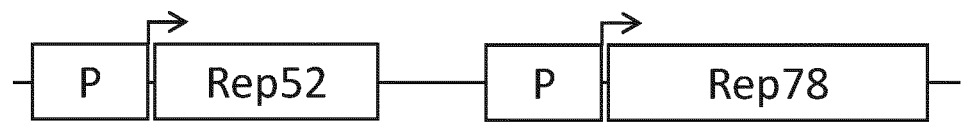
Figure 1:
Figure 1:
Figure 1:
Figure 2A:
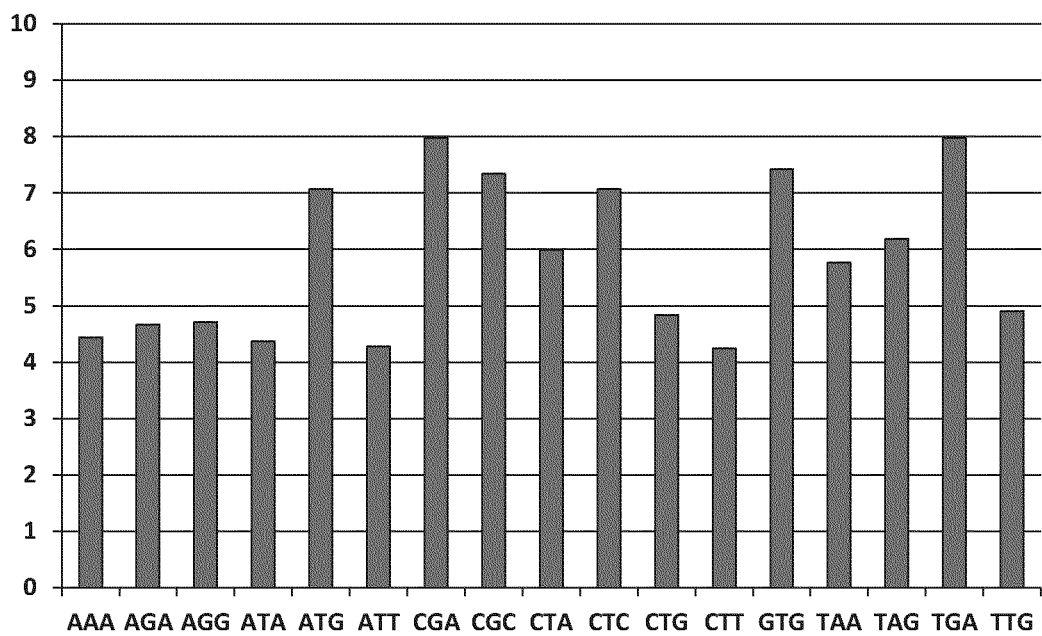
Figure 2B:
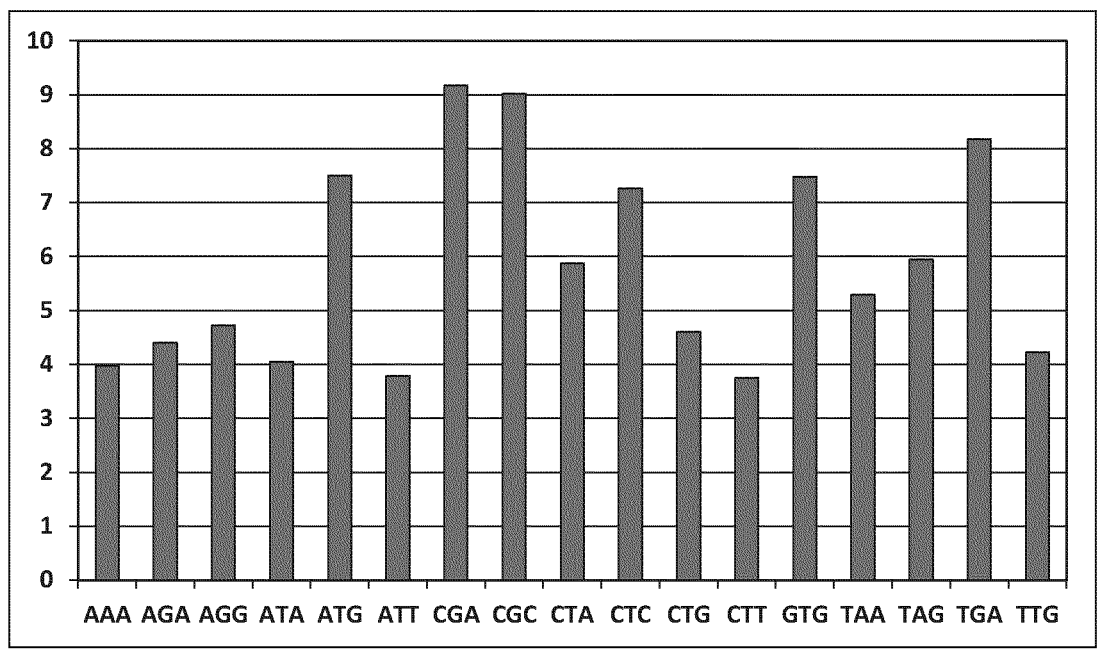
Figure 2C:
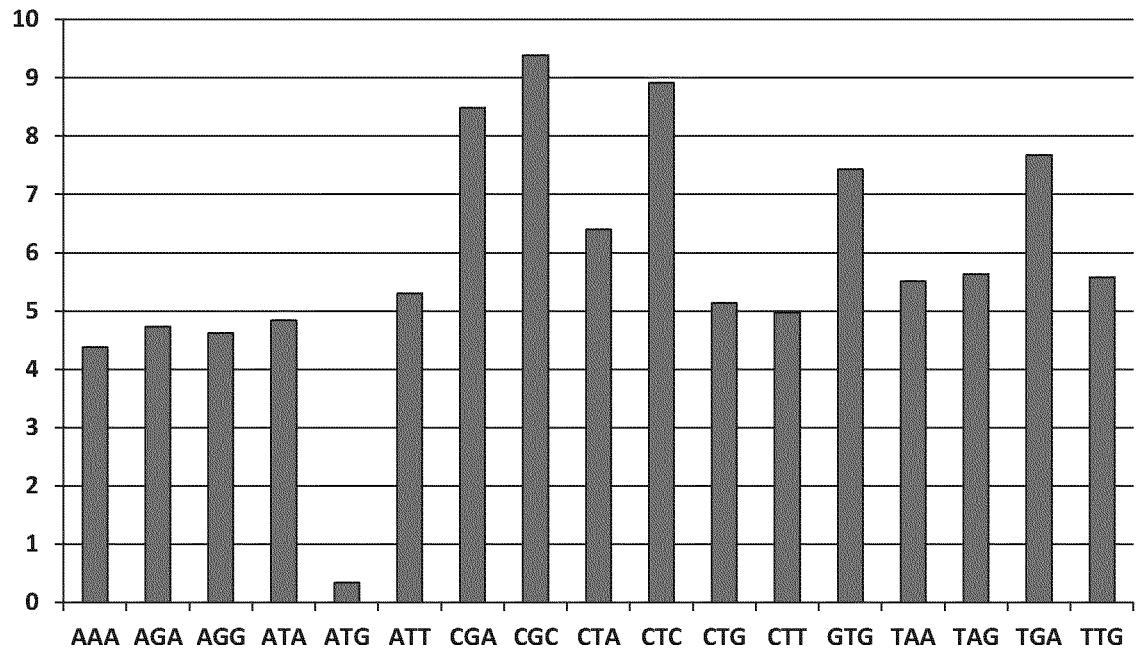
Figure 2D:
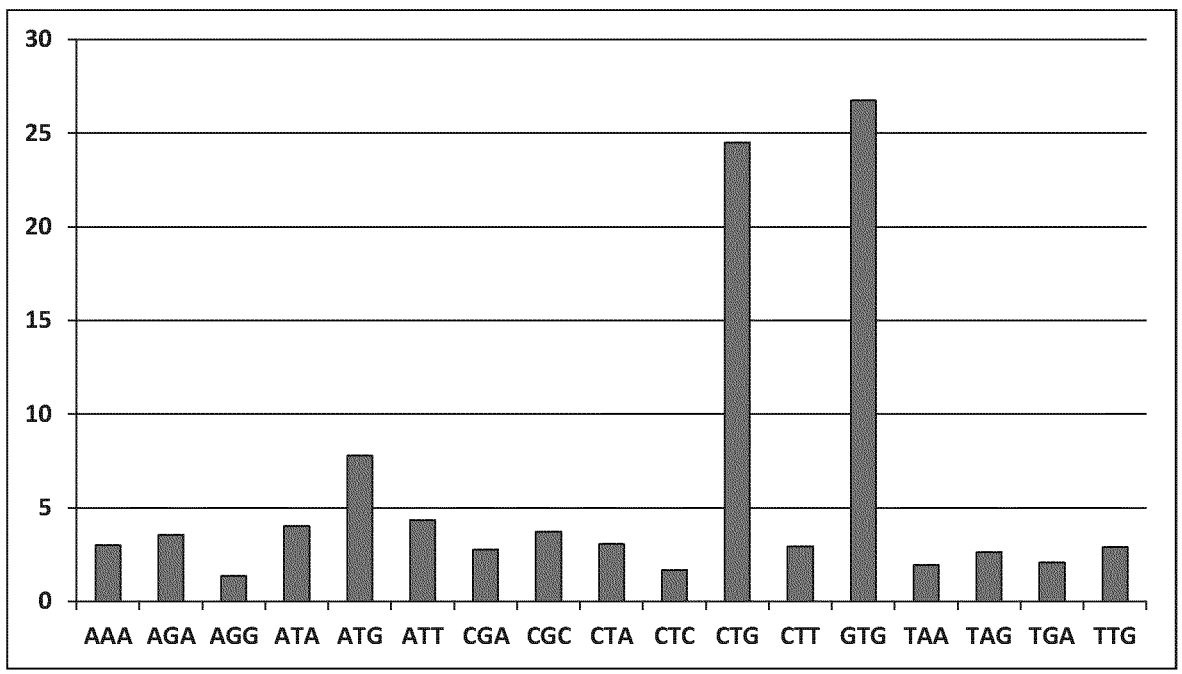
Figure 2E:
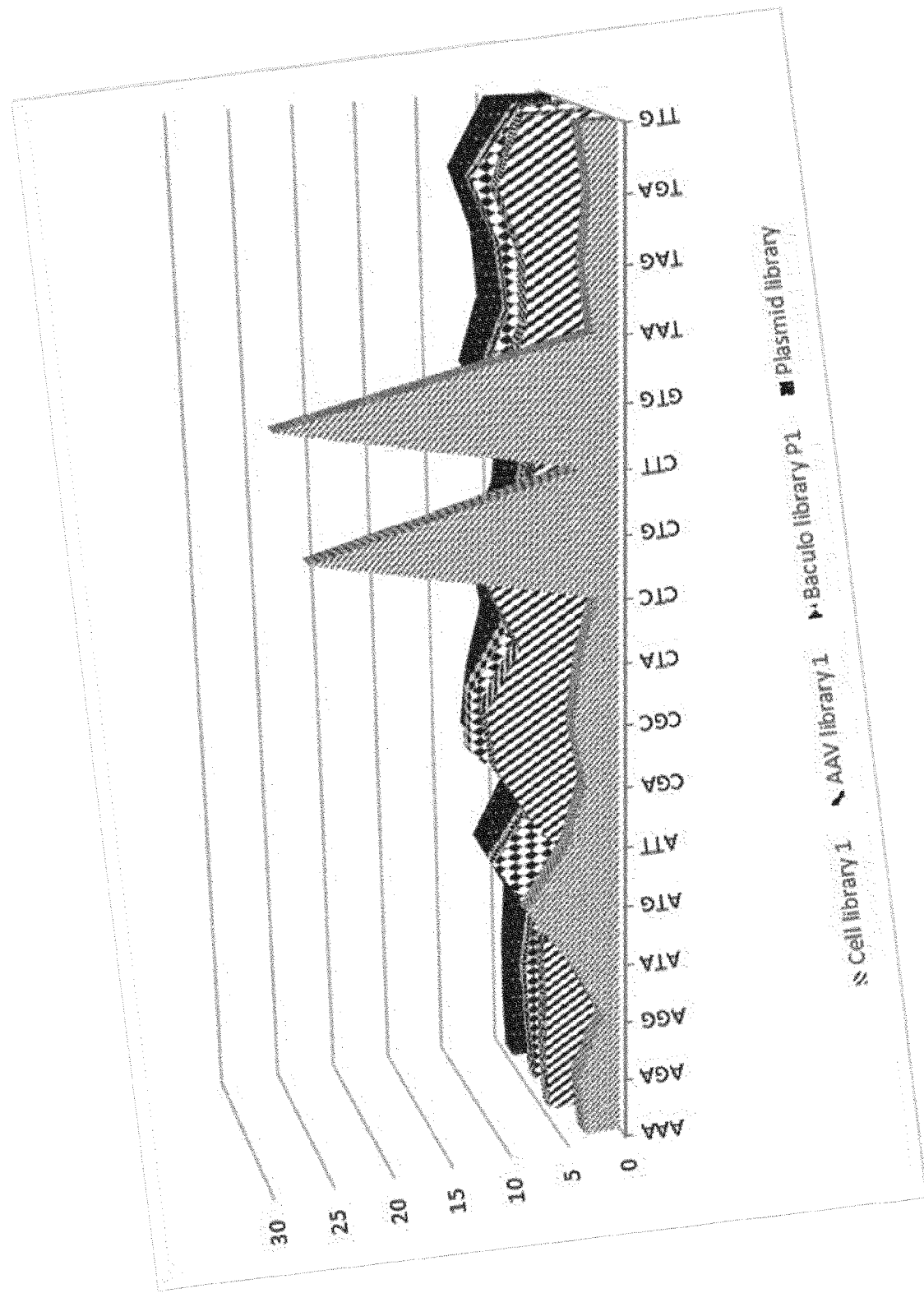

However, in a rational design process a limited subset of constructs and combinations are possible due to the labour-intensive work producing the recombinant baculoviruses. Hence, a library approach was used designing to design a series of alternative start codons (17 in total) in combination with randomized context sequence within the AAV5 capsid in order to determine if there is to still room to select improvements in the quality and yield of the AAV capsid from the BEVS system (see FIG. 1 for the outline of the method). The results and approach depicted below is not limited to AAV5, but can be applied to other serotypes and other parvoviruses as well and can also be used to select for improvements of other features of parvovirus gene therapy vectors as well.

Materials and Methods

Construct Design and Plasmid Library

The following alternative putative start codons across different eukaryotes and prokaryotes were found in literature and utilized as possible start codons for AAV5 VP1 production: ATT, ATG, ATA, AGA, AGG, AAA, CTG, CTT, CTC, CTA, CGA, CGC, TTG, TGA, TAA, TAG and GTG. The construct had the following contextual design: NNN NNN NNN GNN NNN (SEQ ID NO:71). Where NNN indicates the insertion of any of the above start codons for VP1, while N represents A, T, C or G randomly with equal distribution. The "G" in the first trimer following the start codon is fixed. The theoretical complexity of this library is calculated as $7.1 \times 10^7$ ($4^{11} \times 17$), i.e. the maximum number of unique sequences that can be generated. The start codon library was synthesized at GeneArt (ThermoFisher) and the complete sequences with AAV5 encoding capsid sequences and gene expression sequences were cloned into an ITR containing plasmid so that an AAV capsid produced would have the capsid coding gene encapsulated within itself as a transgene. The plasmid library was generated at GeneArt where 100 single colonies from the library were subjected to Sanger sequencing to confirm complexity and diversity within the library.

Baculovirus Library

In order to exploit the power of the BEVS system and thereby screening new designs for their compatibility with the BEVS system, we generated a recombinant baculovirus library from the supplied plasmid library above. The theoretical diversity of the library is $7.1 \times 10^7$. In a standard recombination protocol, we used 1 µg of donor plasmid ($8.12 \times 10^{10}$ plasmid molecules) with 1 µg of Bsu36I digested BacAMT5 baculovirus backbone ($7.34 \times 10^9$ molecules). The limiting factor being the Baculovirus backbone representing the theoretical library complexity 103 times over in case of 100% recombination efficiency. The pooled P0 library was amplified in SF9 cells where it is expected that the baculoviruses amplify approximately 1000-fold resulting in a P1 library representing a full complex library.

AAV Library Generation

For the generation of the AAV library, SF9 cells were inoculated at 1 million cells per ml. MOI (multiplicity of infection) was calculated as follows: MOI=0.7×volume of virus×titre/cell density×volume of cells. We determined that the P1 passage of the Baculovirus library had a titre of approximately $2 \times 10^{11}$ gc/ml. On average the TCID50 values of the baculoviruses are estimated to be about 2 log values below the genome copy titre. Resulting in an estimated TCID50 value of $2 \times 10^9$/ml. The first AAV library (MOI of 0.5) was generated using a calculated infectious titre of $2 \times 10^9$ for the P1 baculovirus library. By inoculating 3 L of insect cells at 1 million cells per ml we have an MOI of 0.5 for the capsid/transgene. In other words, less than one infectious particle per cell. As the capsid is also the transgene, (and therefore capsid) the cassette will be amplified by the replicase approximately 1000-fold per cell. This dual infection is also statistically more efficient with regards to the Poisson distribution when compared to a triple infection. Three further AAV libraries were generated using estimated MOI's of 5, 25 and 50. The AAV library generated with an MOI of 0.5 was found to perform best in the selection method.

Purification and Quantification of AAV

The AAV library material was purified from the 3 L CLB over a 5 ml AVB sepharose column (affinity chromatography) on an Akta Explorer. DNA was isolated and a qPCR was performed on each fraction using primers that amplified an AAV vector genome sequence. From this we pooled fractions for the modified TCID50 assay on HeLa RC32 cells to put selective pressure on the novel mutants in the library. See below. The other three AAV productions (MOI of 5, 25 and 50 respectively) were isolated in a similar fashion. From all isolated AAV libraries DNA was isolated for Next Generation Sequencing (NGS).

Selective Pressure on AAV Library

A modified TCID50 assay on HeLa RC32 cells (Tessier J, et al. J. Virol. 75(1):375-383, 2001) were used to select for AAV variants that displayed the highest potency. HeLa RC32 cells contain the AAV2 replicase and capsid genes incorporated into the genome. Upon transduction with AAV, the transgene is amplified by the replicase and packaged in the AAV capsid that is also generated within the HeLa cell. The advantage of this cell line in principle is that the replicase acts as amplifier of any AAV DNA that enters the nucleus. By performing a limited dilution series of the AAV and infecting the HeLa cells we can selectively amplify only those AAV that manage to reach the nucleus successfully. In other words, select for AAV capsids and constructs that contain/encode for VP1:VP2:VP3 in a good ratio. Dilution series were used for transducing the HeLa cells were: 6400 gc/cell, 3200 gc/cell, 1600 gc/cell, 800 gc/cell, 400 gc/cell and 200 gc/cell.

Isolation of AAV DNA

Two days post-transduction the HeLa cells were lysed and subjected to DNA isolation to recover the AAV vector genomes, of which vector genomes that reached the nucleus are amplified in the HeLa cells. An endpoint PCR using a universal primer set for the capsid library was performed on the isolated DNA before submission to next generation sequencing (NGS).

NGS Sequencing of the Various Libraries

NGS sequencing was performed on isolated DNA from the plasmid library, the P1 passage of the baculovirus library, the productions of the AAV library as well as DNA isolated from the pooled dilutions for each AAV library transduction. Prepared DNA for each sequencing reaction was sent to BaseClear for amplification and barcoding.

Results

An AAV library was generated from a 0.5 MOI infection. Following the production of the AAV library, the library was used for infection of HeLaRC32 cells. The plasmid library, the baculovirus library, the AAV library and the infected HeLaRC32 were processed and analysed for next generation gene sequencing to determine the complexity thereof. Unique sequences were identified at each step and the copy number of each unique sequence was determined as well, the total number of sequences was determined and the relative percentages for each start codon was determined and plotted (see FIGS. 2A-E). The baculovirus library that was generated represented an estimated 74% of the complexity of the plasmid library. Between the plasmid library and baculovirus library there were no striking observations with regard to prevalence of initiation codons (see FIGS. 2A and 2B), which is expected as there is no selection pressure applied thereon. However, when the ATG was used as a start codon, this sequence was found least in AAV capsids (see e.g. FIG. 2C). Here, ATG represents less than 0.5% of the total library. This low percentage was expected, as a strong start codon for VP1 generates mostly VP1 proteins with hardly or no VP2 and VP3 protein production of which VP3 generally is essential to generate capsids. For the remainder, between the plasmid library, the baculovirus library and the AAV capsid library, there were no striking observations made with regard to percentages with regard to codon usage as they were all within a normal range of variation (ranging from about 4-5% to about 8-9%). Finally, the AAV library in general represented approximately 96% of the complexity of the baculovirus library, suggesting a comprehensive transfer of the complexity in the generation of the AAV from the baculovirus library. Finally, when HeLa RC32 cells were infected with the AAV library in a limited dilution series we found that CTG and GTG were the two most abundant start codons for the production of potent AAV viral capsid particles in the baculovirus expression system. CTG and GTG together made up almost 50% of all sequences that successfully transduced and infected the cells (i.e. transferred vector genomic DNA to the nucleus to allow for amplification by the HeLaRC32 cells). Strikingly, although only the codon immediately following the start codon was restricted to G, predominantly the codon after the start codon was found to encode for alanine (not shown), confirming that the trimer coding for Ala may have a preference as a second codon for VP1 expression in insect cells, due to amino acid sequence and/or due to the DNA/RNA sequence. Strikingly, the sequences recovered from the cell suggest only a 5% recovery of the AAV library complexity. This indicates that the selective pressure was significant.

Interestingly, ATG as a start codon is the third highest represented start codon in the isolated DNA from the Hela RC32 cells at about 8% of the complete library. This is in contrast to the representation in the AAV library at only 0.5%. The top thirty of the sequences having a VP1 initiation codon is listed below in table 1, with the most prevalent one listed at the top (SEQ ID NO.1) taking up the majority of the population. Each sequence in itself allows for efficient production of AAV capsids when used as a replacement sequences of the VP1 start codon sequence context. Although each sequence in itself may have some inherent properties that allows for efficient production of AAV capsids, in addition basic features can be identified from the sequences listed below that may describe some general rules governing efficient production of potent AAV from an ATG start codon (see i.a. FIGS. 5A-5D). This can include, but may not necessarily be restricted to, an (out of frame) initiation codon before the VP1 initiation codon, and/or a GT sequence immediately following the ATG codon, resulting in preferably a Valine at position 2 of the VP1 capsid. For the large majority of the 30 clones an upstream out-of-frame start codon that could act as a translational initiation site (ATG, CTG, ACG, TTG and GTG) was observed. Such out-of-frame start codons when translated are expected to result in short peptides having a stop codon after the VP1 initiation codon. Also, out-of-frame CTT or CTC non-canonical start codons can be identified. While CTT and CTC are not regarded as a strong non-canonical start codon we observed that various capsids were isolated from the HeLa cells that contained these two start codons specifically. Without being bound by theory, this suggests that an out-of-frame start codon preceding the VP1 ATG may act as a decoy translational initiation context for the ribosome, thereby interfering with VP1 translation and allowing for pseudo leaky ribosomal scanning as can be observed with wild type AAV. More specifically, the synthesis of (short) peptides from these alternative start codons may allow the ribosome to either continue scanning on the mRNA transcript or cause it to re-initiate. This delay and leaky initiation may allow for the translation of VP2 and VP3 from one polycistronic mRNA transcript. Moreover, this may arguably resemble what happens when CTG, GTG, TTG and ACG are introduced as non-canonical start codons (granted European patent No. 1,945,779 B1; granted U.S. Pat. No. 8,163,543; Urabe et al 2002; supra) thereby allowing ribosomes to regularly not initiate translation at the non-canonical VP1 start codon allowing sufficient initiation of translation of VP2 and VP3 from their respective start codons in the single mRNA transcript.

TABLE 1

The top 30 sequences from the ATG containing clones recovered from the HeLaRC32 cells.

| SEQ ID NO. | DNA sequence |
| --- | --- |
| 69 | CTNNNNNNATGGNNNNNTTT |
| 1 | CTCGATGCATGGTAAGCTTT |
| 2 | CTGAATACATGGTCACCTTT |
| 3 | CTAACTTAATGGTAGCATTT |
| 4 | CTCAATGGATGGTTAGTTTT |
| 5 | CTCGACGTATGGTCACATTT |
| 6 | CTCCCTGAATGGCATTGTTT |
| 7 | CTAGCACGATGGCGTCATTT |
| 8 | CTGACCGCATGGCGACGTTT |
| 9 | CTGGAGATATGGTGAGTTTT |
| 10 | CTTGTTTTATGGTAAGTTTT |
| 11 | CTCAGTTGATGGTCAGCTTT |
| 12 | CTACTTGTATGGTAGCTTTT |
| 13 | CTCGATGCATGGCAAGCTTT |
| 14 | CTGTTAGAATGGCGACGTTT |
| 15 | CTCGACCAATGGGAACGTTT |
| 16 | CTGGCGTCATGGGTCGTTT |
| 17 | CTCGATGCATGGTAAGCTCT |

TABLE 1-continued

The top 30 sequences from the ATG containing clones recovered from the HeLaRC32 cells.

| SEQ ID NO. | DNA sequence |
| --- | --- |
| 18 | CTCGATGCATGGTGAGCTTT |
| 19 | CTCGATGCATGGTAAGCCTT |
| 20 | CTCCTCGGATGGCGTCATTT |
| 21 | CTTGGGCGATGGTTTCATTT |
| 22 | CTAATTGAATGGCGGAGTTT |
| 23 | CTCGATGCATGGTAGGCTTT |
| 24 | CTCGATGCATGGTAAGCTTC |
| 25 | CTTTGCTTATGGTAAATTTT |
| 26 | CTCGACGCATGGTAAGCTTT |
| 27 | CTCACTTGATGGCTTAATTT |
| 28 | CTCAGGGAATGGGATTCTTT |
| 29 | CTTATTCTATGGTAAGTTTT |
| 30 | CTCGGTGCATGGTAAGCTTT |

In order to confirm that the selection process of the library generated useful novel clones, two representative start codon constructs each for ATG, CTG, GTG and one representative construct for TAG and TGA respectively were selected for recombination into a stable baculovirus clone (Table 1). These constructs were used to determine viral capsid subunit ratio's and potency. Moreover, we wanted to confirm that constructs with an ATG start codon generated high yields and potent AAV.

TABLE 2

Unique start codons with their context sequences for baculovirus generation.

| SEQ ID NO. | | |
| --- | --- | --- |
| 74 | AAV5 construct | CTATAAAT<u>ATG</u>GTCTCTTTT |
| 1 | ATG1 | CTCGATGC<u>ATG</u>GTAAGCTTT |
| 31 | ATG2 | CTGTCGTC<u>ATG</u>GTGTCGTTT |
| 63 | CTG1 | CTCGTGCC<u>CTG</u>GCTTCGTTT |
| 64 | CTG2 | CTTGATGT<u>CTG</u>GCCACTTTT |
| 65 | GTG1 | CTTCCACT<u>GTG</u>GCCTCCTTT |
| 66 | GTG2 | CTTCCGCC<u>GTG</u>GCGTCGTTT |
| 67 | TAG1 | CTGCCCCC<u>TAG</u>GACCGTTTT |
| 68 | TGA1 | CTTCACCC<u>TGA</u>GCGCAATTT |

The unique start codon sequences contexts (VP1 initiation codon underlined) were selected and cloned as a replacement in an AAV5 expression construct sequence (SEQ ID NO:70 and 74, wherein SEQ ID NO:74 corresponds to nts. 148-167). SEQ ID NO:31 was a predominant clone selected and identified from the MOI 5 library. Several clones were generated for each candidate and VP capsid expression analysed (FIG. 3). Start codons with their relative context had varying degrees of success in generating AAV capsids with a good stoichiometry. Note that there were in most cases three clones tested per construct to determine whether the baculovirus clone is stable. In this regard, ATG1 had one stable producer (second lane for ATG1 in FIG. 3). For ATG2 there were ample stable producers, all with good stoichiometry. The CTG1 construct failed to produce while CTG2 produced capsids stoichiometry similar as described in International patent application WO2015/137802 (data not shown). Similarly, GTG2 also displayed a good stoichiometry, while TAG (stop codon) produced very low amounts and TGA (a stop codon) resulted in production of a VP1-less capsid. Hence, surprisingly it was confirmed that we were able to generate efficient AAV capsid constructs, i.e. AAV5, wherein ATG was utilized as a start codon displaying a good stoichiometry.

A stable clone for each of the start codon constructs was selected and used to produce AAV harboring the SEAP reporter gene under the control of the CMV promoter. All the AAV constructs produced titers (gc/ml) in a similar range. Following titration, we transduced both Huh7 and HeLa cells at three different MOI's and determined the SEAP activity after 48 hours (FIGS. 5A and 5B). Strikingly, the two constructs with an ATG start codon produced capsids of similar or somewhat improved potency as compared with CTG and GTG whereas the capsid lacking VP1 (TGA) had no discernible SEAP activity above background as expected. Supporting evidence that Valine may improve potency is provided by the fact that dominant unique clones identified in table 1 encode Valine at position 2. These results were in agreement with the observations from FIG. 3 where these capsids displayed a VP1:VP2:VP3 stoichiometry very similar to the CTG and GTG constructs.

What is claimed is:

1. A nucleic acid construct, comprising expression control sequences for expression in an insect cell of a nucleotide sequence comprising an open reading frame (ORF) and, upstream of the ORF, an alternative start codon which is out of frame with the ORF, wherein the open reading frame sequence encodes:
   (i) adeno-associated virus (AAV) capsid proteins VP1, VP2 and VP3; and
   (ii) an ATG translation initiation codon for VP1.

2. The nucleic acid construct according to claim 1, wherein the alternative start codon is selected from the group consisting of CTG, ATG, ACG, TTG, GTG, CTC and CTT.

3. The nucleic acid construct according to claim 2, wherein the nucleotide sequence comprises an alternative open reading frame starting with the alternative start codon that encompasses the ATG translation initiation codon for VP1.

4. The nucleic acid construct according to claim 3, wherein the alternative open reading frame following the alternative start codon encodes a peptide of up to 20 amino acids.

5. The nucleic acid construct according to claim 1, wherein the nucleotide sequence adjacent to the open reading frame and comprising the alternative start codon is nucleotide residues 1-8 of SEQ ID NO. 1.

6. The nucleic acid construct according to claim 5, wherein the open reading frame comprising the ATG translation initiation codon for VP1 has the nucleotide sequence of SEQ ID NO:1, wherein the residues at positions 9-11 represent the ATG translation initiation codon for VP1.

7. The nucleic acid construct according to claim 1, wherein the second codon of the open reading frame encodes an amino acid residue selected from the group consisting of alanine, glycine, valine, aspartic acid and glutamic acid.

8. The nucleic acid construct according to claim 1, wherein the AAV capsid proteins are AAV serotype capsid proteins.

9. The nucleic acid construct according to claim 1, wherein the nucleic acid construct comprises a promoter selected from the group consisting of polyhedron promoter, p10 promoter, 4×Hsp27 EcRE+minimal Hsp70 promoter, deltaE1 promoter and E1 promoter.

10. The nucleic acid construct according to claim 1, wherein the nucleic acid construct is a baculoviral vector.

11. An insect cell comprising a nucleic acid construct according to claim 1.

12. An insect cell according to claim 11, wherein the insect cell further comprises:
   (a) a second nucleotide sequence comprising at least one AAV inverted terminal repeat (ITR) nucleotide sequence;
   (b) a third nucleotide sequence comprising a Rep78 or a Rep68 coding sequence operably linked to expression control sequences for expression in an insect cell; and
   (c) optionally, a fourth nucleotide sequence comprising a Rep52 or a Rep40 coding sequence operably linked to expression control sequences for expression in an insect cell.

13. A method for producing an AAV in an insect cell, comprising:
   (a) culturing an insect cell comprising a nucleic acid construct, comprising expression control sequences for expression in an insect cell of a nucleotide sequence comprising an open reading frame (ORF) and, upstream of the ORF, an alternative start codon which is out of frame with the ORF, wherein the open reading frame sequence encodes:
      (i) adeno-associated virus (AAV) capsid proteins VP1, VP2 and VP3; and
      (ii) an ATG translation initiation codon for VP1,
   under conditions such that AAV is produced; and optionally
   (b) recovery of the AAV.

\* \* \* \* \*